US011376146B2

(12) United States Patent
Fiebig et al.

(10) Patent No.: US 11,376,146 B2
(45) Date of Patent: Jul. 5, 2022

(54) TISSUE INTERFACE FEATURES FOR IMPLANTABLE SPHINCTER ASSISTANCE DEVICE

(71) Applicant: ETHICON LLC, Guaynabo, PR (US)

(72) Inventors: Kevin M. Fiebig, Cincinnati, OH (US); Frederick E. Shelton, IV, Hillsboro, OH (US)

(73) Assignee: Cilag GmbH International, Zug (CH)

( * ) Notice: Subject to any disclaimer, the term of this patent is extended or adjusted under 35 U.S.C. 154(b) by 743 days.

(21) Appl. No.: 16/221,722

(22) Filed: Dec. 17, 2018

(65) Prior Publication Data

US 2020/0188080 A1    Jun. 18, 2020

(51) Int. Cl.
| | | |
|---|---|---|
| *A61F 5/00* | (2006.01) | |
| *A61F 2/04* | (2013.01) | |
| *A61B 17/12* | (2006.01) | |
| *A61B 17/00* | (2006.01) | |
| *A61B 18/00* | (2006.01) | |

(52) U.S. Cl.
CPC ...... *A61F 5/0063* (2013.01); *A61B 17/12099* (2013.01); *A61F 2/04* (2013.01); *A61B 2017/00818* (2013.01); *A61B 2018/00553* (2013.01); *A61F 2002/044* (2013.01); *A61F 2210/009* (2013.01)

(58) Field of Classification Search
CPC .... A61F 2/0004; A61F 2/0031; A61F 2/0036; A61F 2/0077; A61F 2/04; A61F 2002/044; A61F 5/0053; A61F 5/0063; A61B 17/12; A61B 17/12013
See application file for complete search history.

(56) References Cited

U.S. PATENT DOCUMENTS

| | | |
|---|---|---|
| 5,122,136 A | 6/1992 | Guglielmi et al. |
| 5,204,382 A | 4/1993 | Wallace et al. |
| 5,509,888 A | 4/1996 | Miller |
| 5,702,361 A | 12/1997 | Evans, II et al. |
| 6,543,456 B1 | 4/2003 | Freeman |

(Continued)

FOREIGN PATENT DOCUMENTS

| | | |
|---|---|---|
| DE | 3011742 A1 | 10/1981 |
| EP | 1547549 A2 | 6/2005 |

(Continued)

OTHER PUBLICATIONS

U.S. Appl. No. 15/908,875, entitled Laparoscopic Sizing Instrument, filed Mar. 3, 2018.

(Continued)

*Primary Examiner* — Carrie R Dorna
(74) *Attorney, Agent, or Firm* — Frost Brown Todd LLC

(57) ABSTRACT

An implantable sphincter assistance device is configured to surround an exterior wall of an esophagus. The implantable sphincter assistance device includes a plurality of beads, at least one connector, and secondary material. Each of the beads has an exterior surface. The connector is configured to serially connect the beads to form a ring. The secondary material is configured to be disposed between the exterior surface of at least one of the beads and the exterior wall of the esophagus. The secondary material is configured to control remodeling of tissue surrounding the exterior wall of the esophagus.

20 Claims, 16 Drawing Sheets

(56) References Cited

U.S. PATENT DOCUMENTS

| | | | |
|---|---|---|---|
| 6,676,674 B1* | 1/2004 | Dudai | A61B 17/12 606/151 |
| 7,175,589 B2 | 2/2007 | Deem et al. | |
| 7,374,565 B2 | 5/2008 | Hassler, Jr. et al. | |
| 7,390,294 B2 | 6/2008 | Hassler, Jr. | |
| 7,445,010 B2 | 11/2008 | Kugler et al. | |
| 7,481,763 B2 | 1/2009 | Hassler, Jr. et al. | |
| 7,695,427 B2 | 4/2010 | Kugler et al. | |
| 7,727,141 B2 | 6/2010 | Hassler, Jr. et al. | |
| 7,879,068 B2 | 2/2011 | Dlugos et al. | |
| 8,070,670 B2 | 12/2011 | Deem et al. | |
| 8,603,023 B2 | 12/2013 | Albrecht et al. | |
| 8,617,049 B2 | 12/2013 | Dlugos, Jr. et al. | |
| 8,636,751 B2 | 1/2014 | Albrecht et al. | |
| 8,715,157 B2 | 5/2014 | Berg et al. | |
| 8,734,475 B2 | 5/2014 | Ekvall et al. | |
| 8,870,742 B2 | 10/2014 | Dlugos, Jr. et al. | |
| 8,876,761 B2 | 11/2014 | Albrecht et al. | |
| 10,405,865 B2 | 9/2019 | Shelton, IV et al. | |
| 2004/0092892 A1* | 5/2004 | Kagan | A61F 5/0079 604/264 |
| 2005/0049718 A1* | 3/2005 | Dann | A61F 5/0086 623/23.65 |
| 2005/0283235 A1 | 12/2005 | Kugler et al. | |
| 2009/0062824 A1 | 3/2009 | Berg et al. | |
| 2009/0198333 A1* | 8/2009 | Becker | A61F 2/0077 623/8 |
| 2011/0098731 A1 | 4/2011 | Whitbrook et al. | |
| 2013/0053874 A1* | 2/2013 | Ekvall | A61B 17/12013 606/157 |
| 2014/0336696 A1 | 11/2014 | Kugler et al. | |
| 2017/0055986 A1 | 3/2017 | Harris et al. | |
| 2019/0029689 A1 | 1/2019 | Shelton, IV et al. | |

FOREIGN PATENT DOCUMENTS

| | | |
|---|---|---|
| WO | WO 1993/015721 A1 | 8/1993 |
| WO | WO 1993/016658 A1 | 9/1993 |
| WO | WO 1993/019702 A1 | 10/1993 |
| WO | WO 1997/033632 A2 | 9/1997 |
| WO | WO 1998/044965 A1 | 10/1998 |
| WO | WO 2000/054835 A1 | 9/2000 |
| WO | WO 2001/047431 A2 | 4/2001 |

OTHER PUBLICATIONS

U.S. Appl. No. 15/914,381, entitled "Tunable Magnetic Sphincter Augmentation Device," filed Mar. 7, 2018.

U.S. Appl. No. 15/914,407, entitled "MRI Compatible Magnetic Sphincter Augmentation Device," filed Mar. 7, 2018.

\* cited by examiner

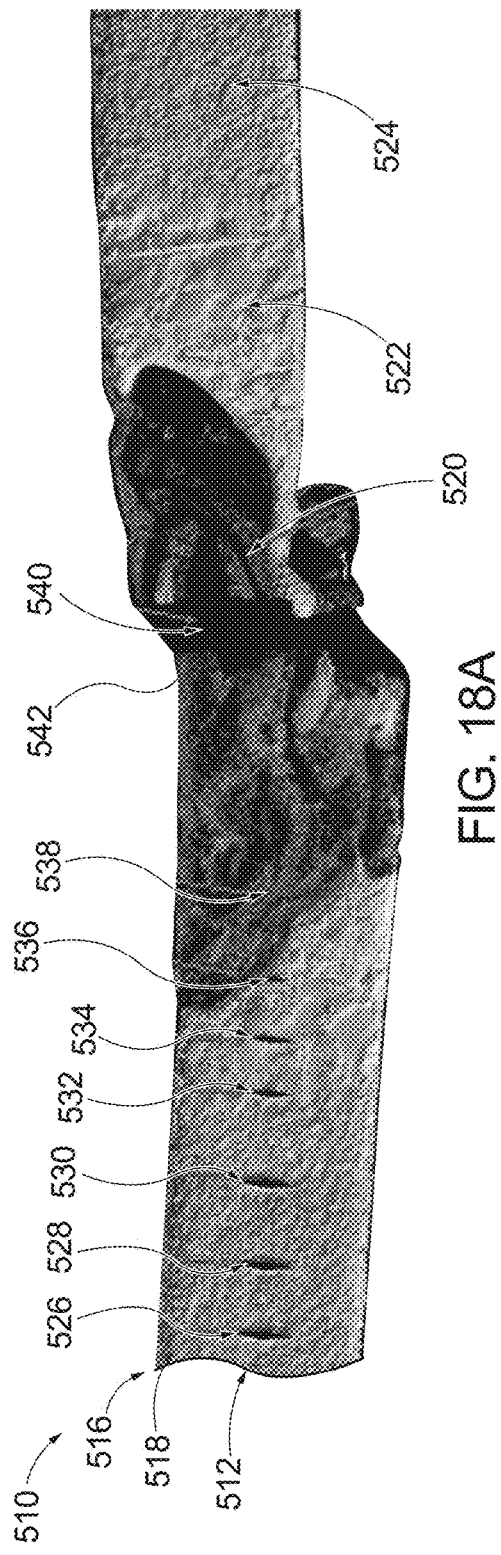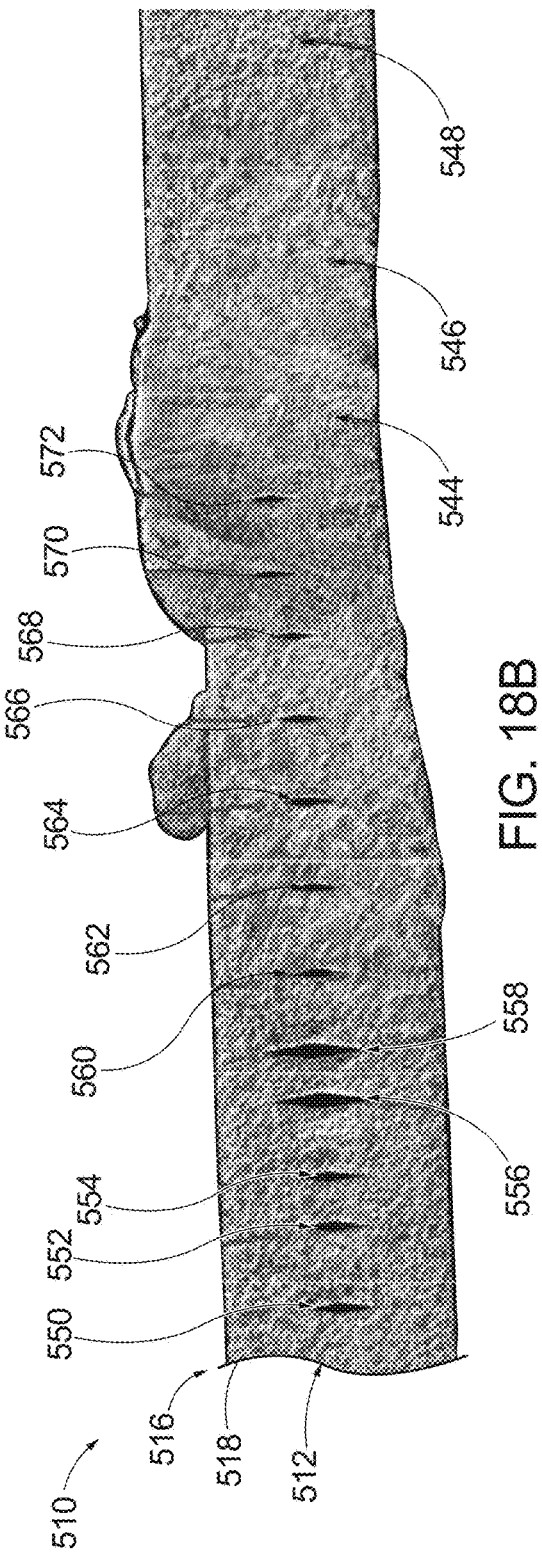

TISSUE INTERFACE FEATURES FOR IMPLANTABLE SPHINCTER ASSISTANCE DEVICE

BACKGROUND

In some instances, it may be desirable to place a medical implant within or surrounding a biological lumen/passageway in order to improve or assist the function of, or otherwise affect, the biological lumen/passageway. Examples of such biological lumens/passageways include, but are not limited to, the esophagus, a fallopian tube, a urethra, or a blood vessel. Some biological passages normally function by expanding and contracting actively or passively to regulate the flow of solids, liquids, gasses, or a combination thereof. The ability of a biological passage to expand and contract may be compromised by defects or disease. One merely illustrative example of a condition associated with decreased functionality of a body passage is Gastro Esophageal Reflux Disease ("GERD"), which effects the esophagus.

A normal, healthy, esophagus is a muscular tube that carries food from the mouth, through the chest cavity and into the upper part of the stomach. A small-valved opening in the esophagus, called the lower esophageal sphincter ("LES"), regulates the passage of food from the esophagus into the stomach, as well as the passage of acidic fluids and food from the stomach toward the esophagus. The LES may also regulate stomach intra-gastric pressures. A healthy LES may contain pressure of gasses within the stomach at around 10 mm Hg greater than normal intragastrical pressure, thereby impeding acidic gases/fluids from refluxing from the stomach back into the esophagus. When functioning properly, a pressure difference greater than 10 mm Hg may regulate when the LES opens to allow gasses to be vented from the stomach toward the esophagus.

If the LES relaxes, atrophies, or degrades for any reason, the LES may cease functioning properly. Therefore, the LES may fail to sufficiently contain pressure of gasses within the stomach such that acidic contents of the stomach may travel back into the esophagus, resulting in reflux symptoms. Two primary components that control the LES are the intrinsic smooth muscle of the distal esophagus wall and the skeletal muscle of the crural diaphragm or esophageal hiatus. A causation of esophageal reflux, which may be associated with GERD, is relaxation of one or both of the smooth muscle of the distal esophagus wall or the hiatal diaphragm sphincter mechanisms. Chronic or excessive acid reflux exposure may cause esophageal damage. Conventionally, treatment for GERD may involve either open or endoscopic surgical procedures. Some procedures may include a fundoplication that mobilizes of the stomach relative to the lower esophagus, or suturing a pleat of tissue between the LES and the stomach to make the lower esophagus tighter.

Examples of devices and methods that have been developed to treat anatomical lumens by providing sphincter augmentation are described in U.S. Pat. No. 7,175,589, entitled "Methods and Devices for Luminal and Sphincter Augmentation," issued Feb. 13, 2007, the disclosure of which is incorporated by reference herein; U.S. Pat. No. 7,695,427, entitled "Methods and Apparatus for Treating Body Tissue Sphincters and the Like," issued Apr. 13, 2010, the disclosure of which is incorporated by reference herein; U.S. Pat. No. 8,070,670, entitled "Methods and Devices for Luminal and Sphincter Augmentation," issued Dec. 6, 2011, the disclosure of which is incorporated by reference herein; and U.S. Pat. No. 8,734,475, entitled "Medical Implant with Floating Magnets," issued May 27, 2014, the disclosure of which is incorporated by reference herein.

While various kinds and types of instruments have been made and used to treat or otherwise engage anatomical lumens, it is believed that no one prior to the inventors has made or used an invention as described herein.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 18A depicts an enlarged sectional view of a bead that is coated without the use of a shielding gas; and FIG. 18B depicts an enlarged sectional view of a bead that is coated with the use of a shielding gas.

Figure 1:
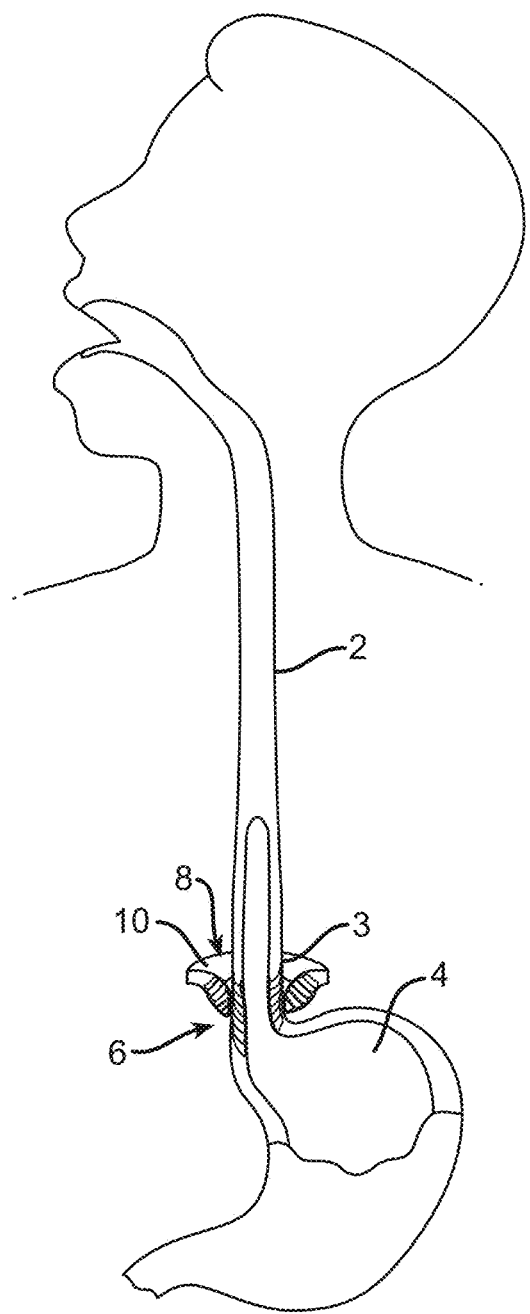
FIG. 1 depicts a cross-sectional side view, taken along a coronal plane of the body, of a biological passage.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Implantable Sphincter Assistance Device

Figure 2:
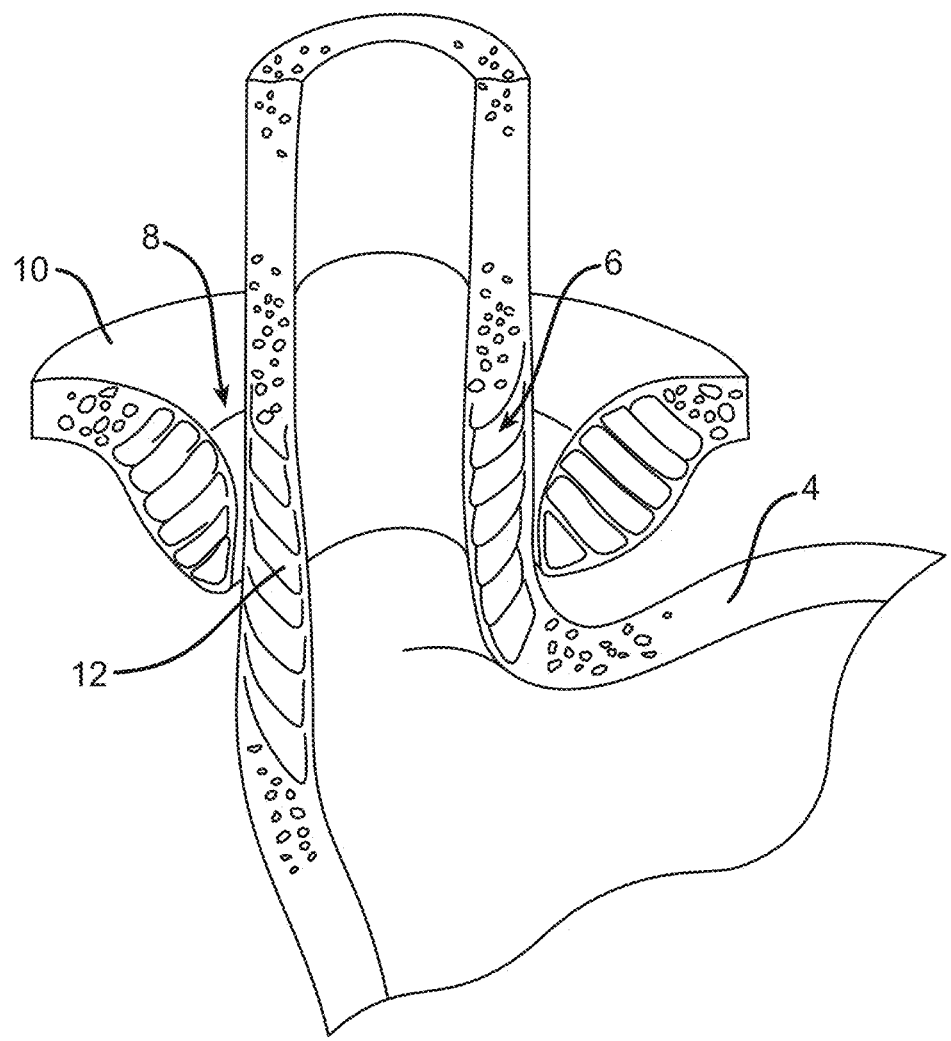
FIG. 2 depicts a cross-sectional isometric view, taken along a coronal plane of the body, of a human esophagogastric junction.
Figure 3:
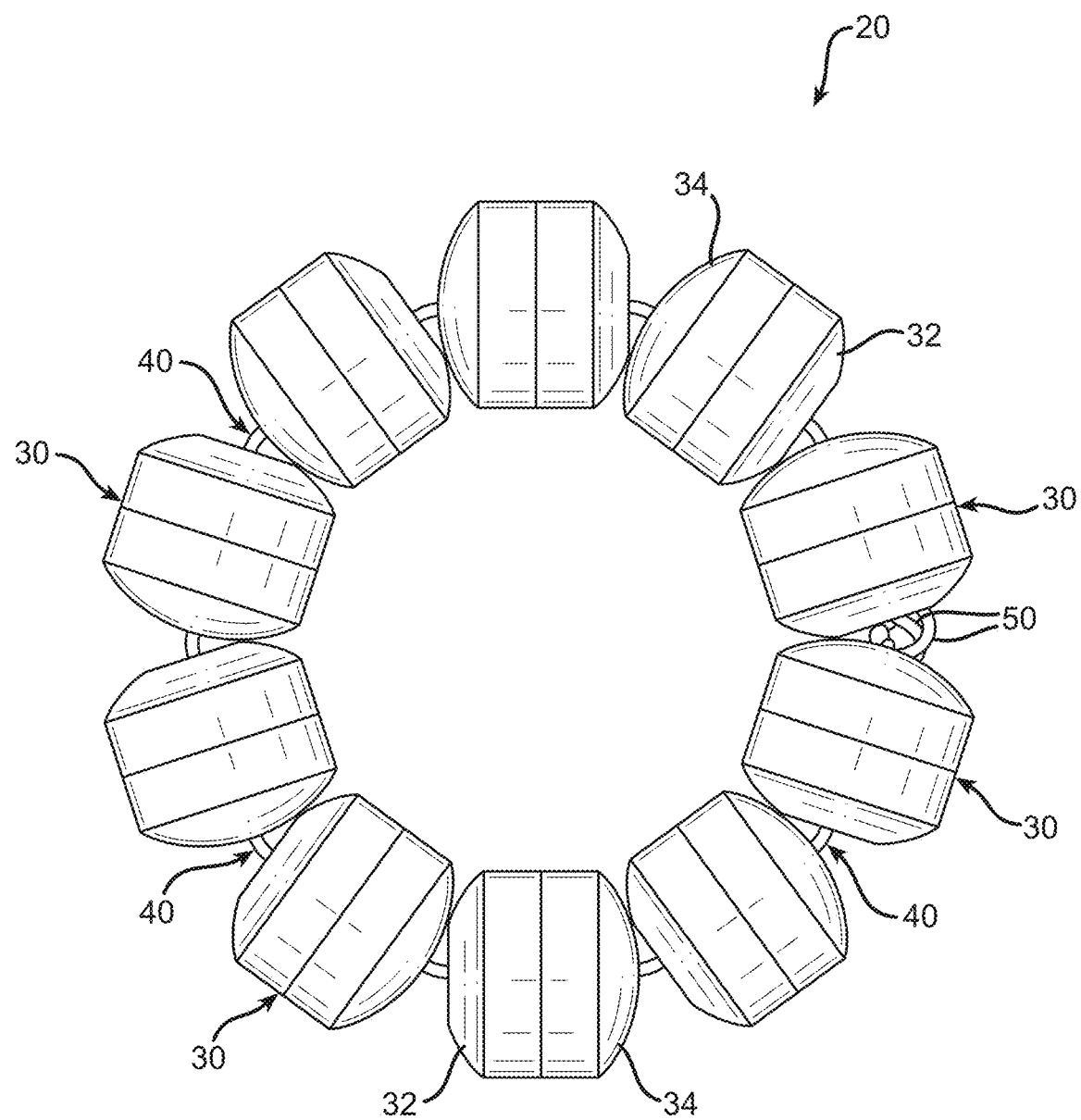
FIG. 3 depicts a top plan view of an exemplary implantable sphincter assistance device.

FIGS. 1-2 show selected portions of human anatomy, which includes an esophagus (2) extending from the mouth, through a hiatus (8) defined by a diaphragm (10), and into a stomach (4). Esophagus (2) also includes a distal esophagus (3) and an LES (6). LES (6) is located along distal esophagus (3) adjacent to the junction of esophagus (2) and stomach (4). The portion of LES (6) extending through hiatus (8) is supported by diaphragm (10). When functioning properly, LES (6) is configured to transition between an occluded state and an opened state (as shown in FIG. 2). As best seen in FIG. 2, LES (6) includes a plurality of sling fibers (12). Sling fibers (12) are smooth muscle tissue that may help regulate LES (6) transition between the occluded state and the open state. Hiatus (8) of diaphragm (10) may also help LES (6) transition between the occluded state and the open state.

A healthy LES (6) transitions between the occluded state and the opened state to act as a valve. In other words, a healthy LES (6) may transition from the occluded state to the opened state to allow solids, liquids, and/or gasses to selectively travel between esophagus (2) and stomach (4). For example, a healthy LES (6) may transition from the occluded state to the opened state to permit a bolus of food to travel from esophagus (2) into stomach (4) during peristalsis; or to vent intra-gastric pressure from stomach (4) toward esophagus (2). Additionally, in the occluded state, a healthy LES (6) may prevent digesting food and acidic fluid from exiting stomach (4) back into esophagus (2).

If LES (6) ceases functioning properly by prematurely relaxing, and thereby improperly transitioning esophagus (2) from the occluded state to the opened state, undesirable consequences may occur. Examples of such undesirable consequences may include acidic reflux from stomach (4) into esophagus (2), esophageal damage, inflamed or ulcerated mucosa, hiatal hernias, other GERD symptoms, or other undesirable consequences as will be apparent to one having ordinary skill in the art in view of the teachings herein. Therefore, if an individual has an LES (6) that prematurely relaxes, causing improper transitions from the occluded state to the opened state, it may be desirable to insert an implant around a malfunctioning LES (6) such that the implant and/or LES (6) may properly transition between the occluded state and the opened state.

Figure 4:
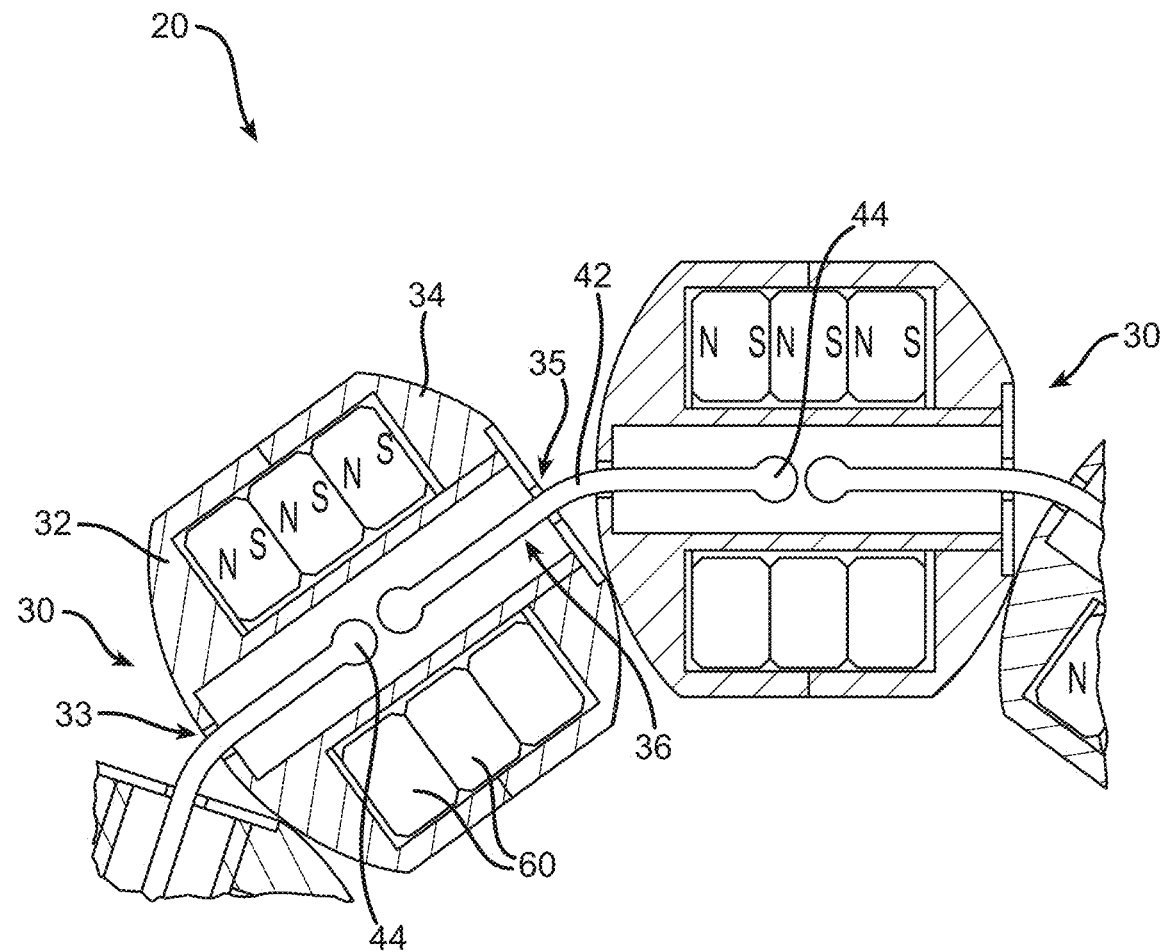
FIG. 4 depicts a partial, cross-sectional view of a portion of the implantable sphincter assistance device of FIG. 3.

FIGS. 3-5B show an exemplary implantable sphincter assistance device (20) that may be used as an implant around a malfunctioning LES (6) to assist the LES (6) in transitioning between the occluded state and the opened state. Device (20) of this example comprises a plurality of beads (30) that are joined together by a plurality of links (40). Each bead (30) comprises a pair of housings (32, 34) that are securely fastened to each other. By way of example only, housings (32, 34) may be formed of a non-ferrous material (e.g., titanium, plastic, etc.). Each bead (30) further comprises a plurality of annular or toroidal rare-earth permanent magnets (60) that are stacked next to each other within housings (32, 34). In the present example, magnets (60) are completely sealed within beads (30). As best seen in FIG. 4, each bead (30) also defines a chamber (36) that is configured to receive a portion of a respective pair of links (40). Housing (32) defines an opening (33) at one end of chamber (36); while housing (34) defines an opening (35) at the other end of chamber (36).

Each link (40) of the present example comprises a wire (42) that is pre-bent to form an obtuse angle. The free end of each wire (42) terminates in a ball tip (44). Beads (30) are joined together by links (40) such that a first end portion of a link (40) is in one bead (30), a second end portion of the same link (40) is in another bead (30), and an intermediate portion of the same link (40) is positioned between those two beads (30). Chambers (36) of beads (30) are configured to freely receive ball tips (44) and adjacent regions of wires (42); while openings (33, 35) are configured to prevent ball tips (44) from exiting chambers (36). Openings (33, 35) are nevertheless sized to allow wire (42) to slide through openings (33, 35). Thus, links (40) and beads (30) are configured to allow beads (30) to slide along length of links (40) through a restricted range of motion.

Figure 5A:
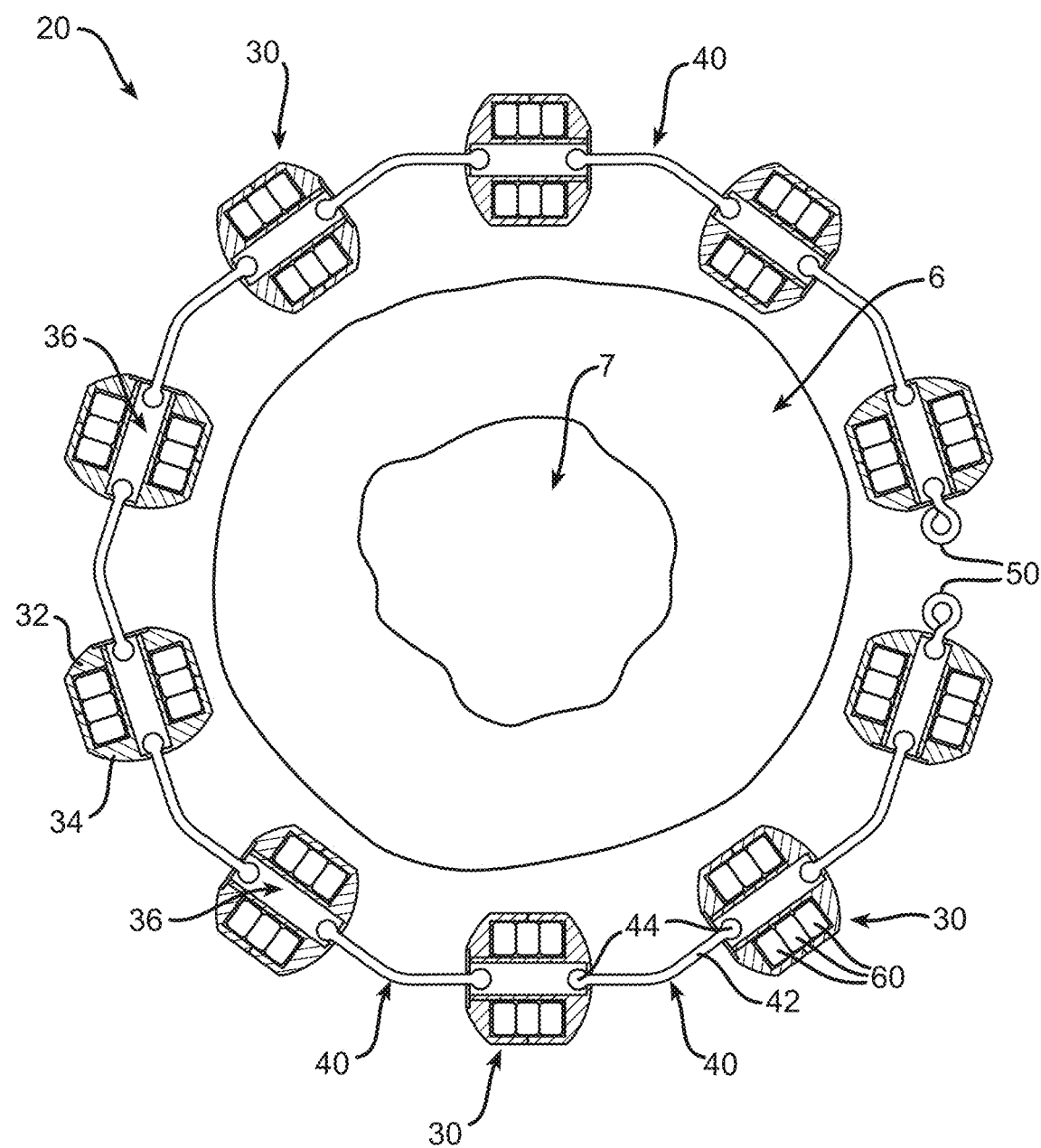
FIG. 5A depicts a top, cross-sectional view of the implantable sphincter assistance of FIG. 3 positioned about an LES, with the implantable sphincter assistance device in an open and expanded configuration.
Figure 5B:
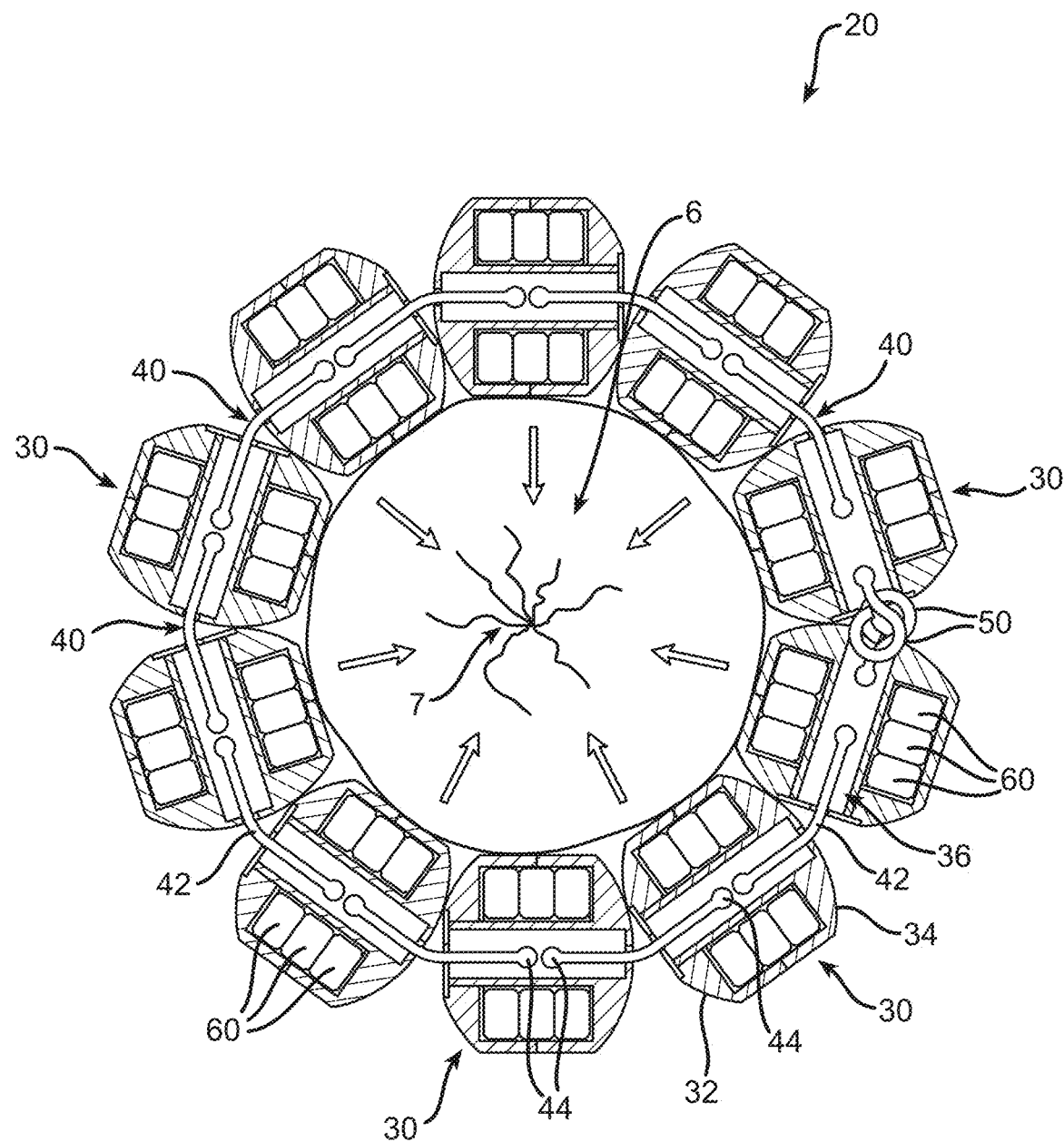
FIG. 5B depicts a top, cross-sectional view of the implantable sphincter assistance device of FIG. 3 positioned about the LES of FIG. 5A, with the implantable sphincter assistance device in a closed and contracted configuration.

As best seen in FIGS. 5A-5B, two beads (30) have opposing fastener features (50) that allow the ends of device (20) to be coupled together to form a loop. In the present example, fastener features (50) comprise eyelets. In some other versions, fastener features (50) comprise complementary clasp features. As another merely illustrative example, fastener features (50) may be configured and operable in accordance with one or more of the teachings of U.S. patent application Ser. No. 15/664,665, entitled "Method for Assisting a Sphincter," filed Jul. 31, 2017, issued as U.S. Pat. No. 10,405,865 on Sep. 10, 2019, the disclosure of which is incorporated by reference herein. Other suitable ways in which the ends of device (20) may be coupled together to form a loop will be apparent to those of ordinary skill in the art in view of the teachings herein. Those of ordinary skill in the art will also recognize that it may be desirable to provide fastener features (50) that can be decoupled if it becomes necessary or otherwise warranted to remove device (20) from the patient.

FIG. 5A shows device (20) in an open, expanded state, with device (20) being positioned about LES (6). At this stage, the opening (7) defined by LES (6) is in a persistently open state (e.g., allowing the patient to undesirably experience GERD and/or other undesirable conditions), warranting the securement of device (20) about the LES (6). FIG. 5B shows device (20) secured about the LES (6), with device (20) in a closed, contracted state. Device (20) is secured closed via fastener features (50). Magnets (60) are oriented within beads (30) such that each bead (30) will be magnetically attracted to the adjacent bead (30) in device (20). In other words, beads (30) are magnetically attracted to each other to magnetically bias device (20) toward the contracted configuration shown in FIG. 5B.

With device (20) secured around the LES (6) and in the contracted configuration, device (20) deforms the LES (6) radially inwardly to substantially close the opening defined by the LES (6). In doing so, device (20) prevents the patient from experiencing GERD and/or other undesirable conditions that may be associated with a persistently open opening (7) at the LES (6). While magnets (60) have a tesla value that is high enough to substantially maintain opening (7) in a closed state to the point of preventing GERD and/or other undesirable conditions that may be associated with a persistently open opening (7), the tesla value of magnets (60) is low enough to allow LES (6) to expand radially outwardly to accommodate passage of a bolus of food, etc. through the opening (7) of LES (6). To accommodate such expansion, beads (30) may simply slide along links (40) to enlarge the effective diameter of device (20) as the bolus passes. After the bolus passes, the magnetic bias of magnets (60) will return device (20) to the contracted state shown in FIG. 5B. Device (20) thus ultimately prevents GERD and/or other undesirable conditions that may be associated with a persistently open opening (7); while still permitting the normal passage of food, etc. from the esophagus (2) to the stomach (4).

In addition to the foregoing, device (20) may be constructed and operable in accordance with at least some of the teachings of U.S. Pat. No. 7,695,427, the disclosure of which is incorporated by reference herein; and/or U.S. patent application Ser. No. 15/664,665, entitled "Method for Assisting a Sphincter," filed Jul. 31, 2017, issued as U.S. Pat. No. 10,405,865 on Sep. 10, 2019, the disclosure of which is incorporated by reference herein.

II. Exemplary Alternative Implantable Sphincter Assistance Devices

When sufficient pressure is applied to tissue for a prolonged time (days to weeks or longer) by an implantable sphincter assistance device, in some instances the tissue may begin to remodel around the device causing the implantable sphincter assistance device to erode through the exterior wall of the tissue/organ (e.g. esophagus). In some cases, this erosion may continue until the pressure is relieved to a level below the level that causes the tissue damage; or the device erodes completely through the exterior wall of the tissue/organ. One approach to prevent this erosion, may be to broaden the surface area over which the force is applied to a level sufficient to bring the pressure below the tissue threshold. Additionally, coatings, absorbable materials, or treatments for devices could toughen the interface between the device and the tissue (e.g., promote growth of scar tissue) to raise the threshold of the pressure before erosion occurs. Likewise, since prolonged pressure may be needed to induce this remodeling, the length of time a pressure is applied could be used to influence the erosion characteristics of the device. To solve these and other problems, the below-described exemplary implantable sphincter assistance devices (110, 210, 310, 410, 510) include secondary material (116, 216, 316, 416, 516) that at least partially surrounds beads (112, 212, 312, 412, 512).

A. First Exemplary Alternative Implantable Sphincter Assistance Device

Figure 6:
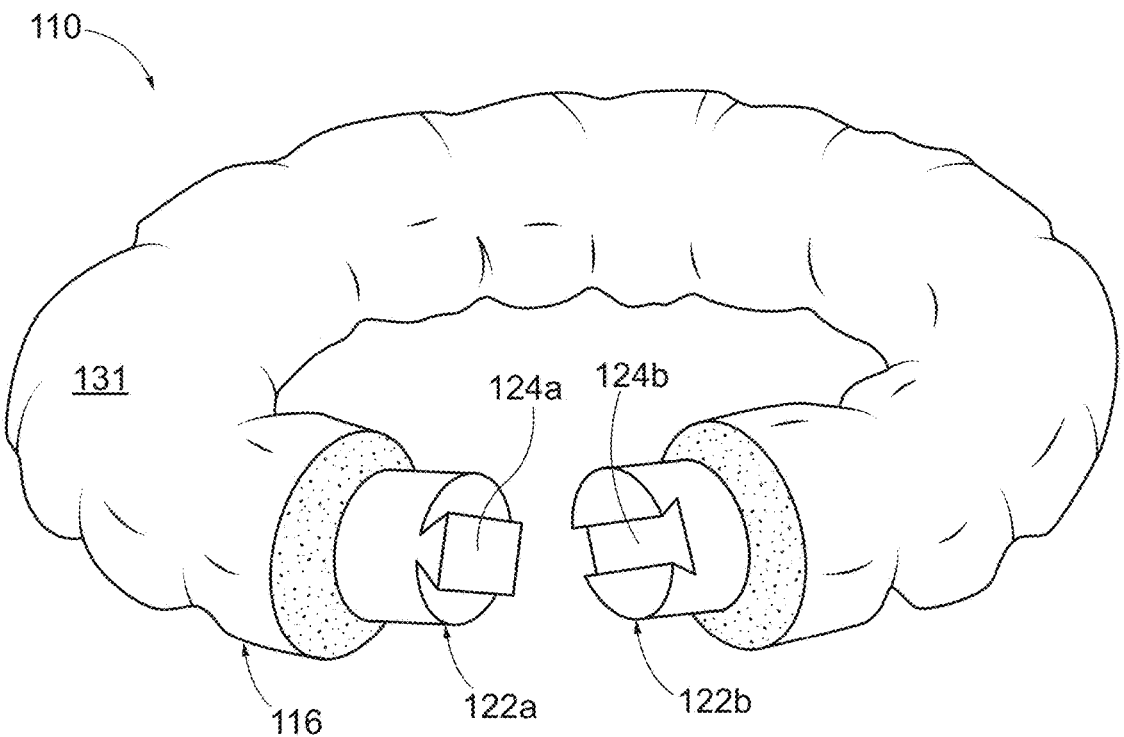
FIG. 6 depicts a perspective view of a first exemplary alternative implantable sphincter assistance device, where the implantable sphincter assistance device includes a bioabsorbable casing disposed around a plurality of beads.
Figure 7:
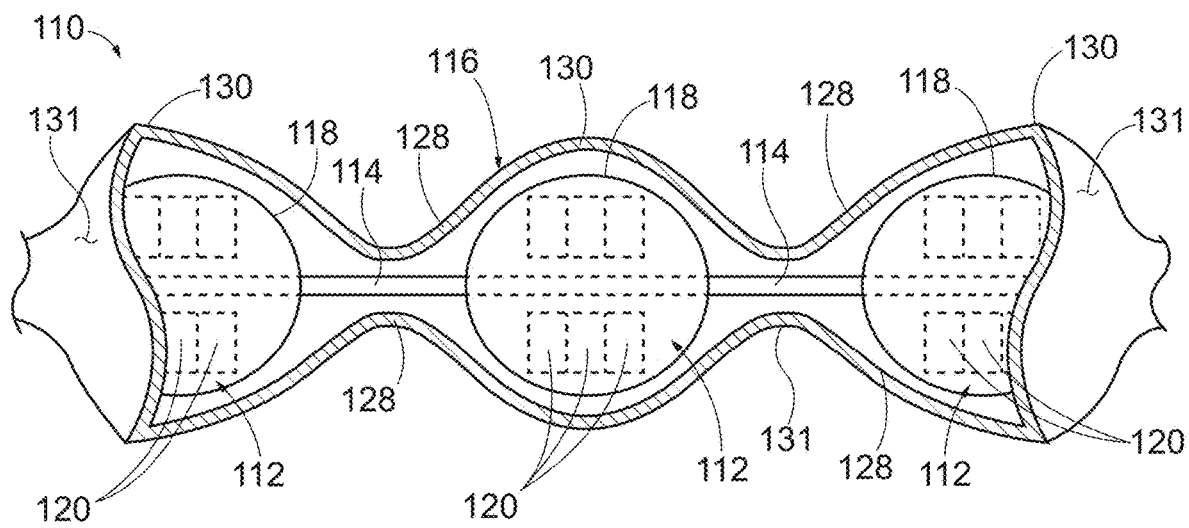
FIG. 7 depicts a cross-sectional view of a portion of the sphincter assistance device of FIG. 6 exposing the beads and flexible wire.

FIGS. 6-8B show a first exemplary alternative implantable sphincter assistance device (110). Device (110) is sized and configured to surround an exterior wall (14) of LES (6). As shown in FIGS. 6 and 7, device (110) includes a plurality of beads (112), at least one connector (shown as flexible wire (114)), and secondary material (116) that at least partially surrounds beads (112). Beads (112) may be similar to beads (30) shown and described above with reference to FIGS. 3-5B. Each bead (112) includes an exterior surface (118) which may be similar to the exterior surface of housings (32, 34) shown and described above with reference to FIGS. 3-5B. Beads (112) are shown as titanium beads; however, beads (112) may be formed from a variety of suitable materials. Beads (112) are configured to be individually moveable along flexible wire (114). For example, each bead (112) may be individually selectively moveable to a desired location. Each bead (112) includes a plurality of magnets (120) configured to impart a radially inwardly oriented magnetic bias. Similar to magnets (60) shown and described above with reference to FIGS. 4-5B, magnets (120) may be annular or toroidal rare-earth permanent magnets or another suitable magnet. Magnets (120) of beads (112) are configured to magnetically bias opening (7) of LES (6) to a closed configuration. Magnets (120) of beads (112) are also configured to permit separation of beads (112) to thereby permit passage of a bolus through opening (7) of LES (6).

As shown in FIG. 6, device (110) also includes first and second clasps (122a-b) that are configured to transition between an unlocked configuration allowing for insertion and removal of device (110) to a locked configuration that radially surrounds LES (6). First and second clasps (122a-b) may be similar to fastener features (50) shown and described above with reference to FIGS. 5A-5B. First and second clasps (122a-b) include complementary attachment portions (124a-b) that are configured to interlock with each other in the locked configuration. As shown, complementary attachment portions (124a-b) are configured to directly connect each other to lock device (110) around tissue. Device (110) also includes flexible wire (114) that is configured to serially connect beads (112) to form a ring (generally shown in FIG. 5B with reference to device (20)). The precise number of beads (112) utilized may vary by patient. While not shown, spacers may be placed between adjacent beads if desired. It is envisioned that flexible wire (114) may include a plurality of links (e.g. links (40) shown and described above with reference to FIGS. 4-5B) or any other suitable connector.

Figure 8A:
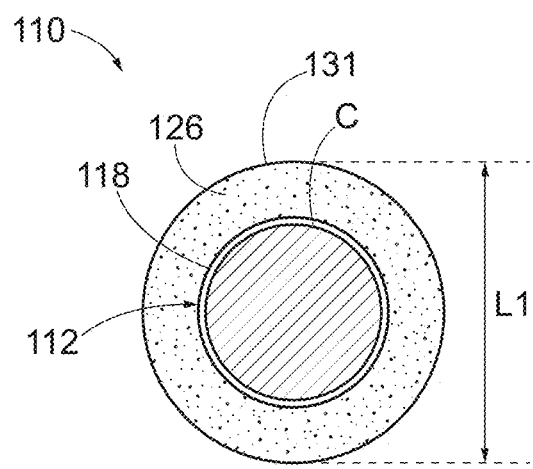
FIG. 8A depicts a cross-sectional view of the implantable sphincter assistance device of FIG. 6 with a bead surrounded by the bioabsorbable casing.

As shown in FIGS. 6-8A, secondary material (116) comprises a bioabsorbable casing (126). As shown in FIG. 7, bioabsorbable casing (126) includes a tapered lead in portion (128) and a raised body portion (130) surrounding a primary circumference (C) (see FIG. 8) of beads (112). Bioabsorbable casing (126) is configured to control remodeling of tissue surrounding exterior wall (11) of LES (6). Bioabsorbable casing (126) may be applied to flexible wire (114) and exterior surface (118) beads (112). Moreover, bioabsorbable casing (126) is coupled with exterior surface (118) of at least one of beads (112). It is also envisioned that bioabsorbable casing (126) may be coupled with exterior surface (118) of a majority of beads (112) or even every bead (112). As used herein, majority is intended to mean more than half. Bioabsorbable casing (126) extends radially outwardly from exterior surface (118) of beads (112). FIG. 8A shows a sectional view of device (110) of FIG. 6, with bead (112) surrounded by bioabsorbable casing (126). Bioabsorbable casing (126) includes an exterior surface (131) that defines a first length (L1) which is shown as the diameter of bioabsorbable casing (126). While FIGS. 7 and 8 show bead (112) having a solid cross-section, it is also envisioned that interior of bead (112) may be similar to the interior of bead (30) shown in FIGS. 4-5B. Bioabsorbable casing (126) is configured to be disposed between exterior surface (118) of at least one of beads (112) and exterior wall (11) LES (6).

Figure 8B:
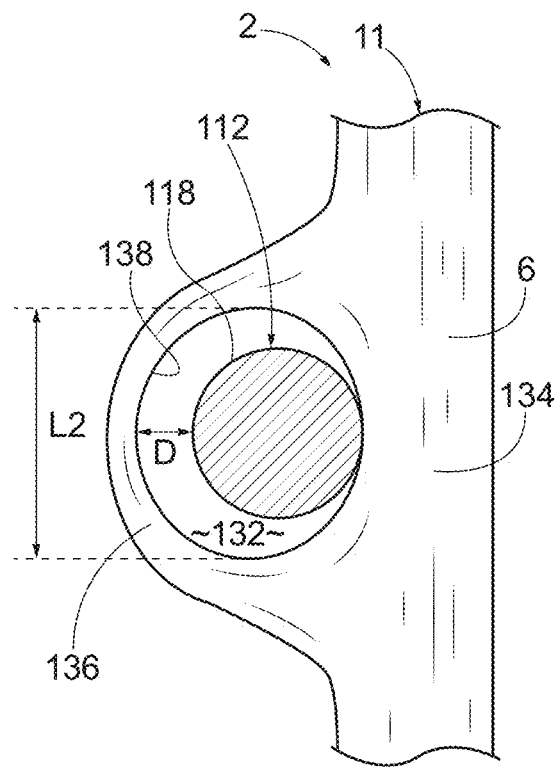
FIG. 8B depicts a cross-sectional view of the implantable sphincter assistance device of FIG. 8A implanted into an external wall of the LES, with the bioabsorbable casing absorbed by the exterior wall of the LES to form a tissue capsule.

FIG. 8B shows a sectional view of device (110) implanted into exterior wall (11) of LES (6). As shown, bioabsorbable casing (126) is already absorbed by exterior wall (11) of LES (6) to form a tissue capsule (132) having a second length (L2) that is smaller than first length (L1). However, second length (L2) may be greater than or the same size as first length (L1). Exterior wall (11) includes inner wall portion (134) and outer wall portion (136). Tissue capsule (132) is configured to have an inner surface (138) that is separated a distance (D) from bead (112) allowing beads (112) to freely move around inside tissue capsule (132). Bioabsorbable casing (126) may be disposed between exterior surface (118) of at least a majority of beads (112) (or every bead (112)) and exterior wall (11) of LES (6). Bioabsorbable casing (126) is absorbed by exterior wall (11) of LES (6) creating tissue capsule (132) having a greater cross-sectional volume than device (110) now that bioabsorbable casing (126) is absorbed into LES (6). The greater volume allows for movement of beads (112) to help prevent tissue erosion.

As such, features on the inner diameter or outer diameter of beads (112) have tissue interaction aspects and control the interface between tissue capsule (132) and beads (112) to increase the free operating space of bead (112) and minimize interaction with the encapsulation. Features integrated into the perimeter (e.g. circumference (C)) of bioabsorbable casing (126) encourage the remodeling encapsulation to be more open to movement of beads (112). External arc features that create tissue capsule (132) defines tissue capsule (132) over device (110). Features may extend from the exterior of the arc outward or laterally enabling device (110) to better define tissue capsule (132) hat remodels around the outer diameter of device (110). These features may be interlocking, space occupying, or tissue interactive. Features may be on either the outer diameter or the inner diameter of device (110) encourages tissue capsule (132) that forms around device (110) to be bigger than the diameter of device (110). As previously described with reference to FIG. 7, device (110) includes raised body portion (130) of the primary circumference of bead (112) with gradual tapered lead in portion (128) slopes to either side of device (210). This causes bead (112) to naturally wedge itself through tissue capsule (132) with each expansion and contraction straining the tubular diameter of the forming tissue capsule (132) and encourage tissue capsule (132) to have a greater inner diameter than the outer diameter of device (110) as shown in FIG. 8B. This also encourages inner surface (138) of tissue capsule (132) to be radially expandable due the force loading on the tissue during healing with each expansion.

B. Second Exemplary Alternative Implantable Sphincter Assistance Device

Figure 9:
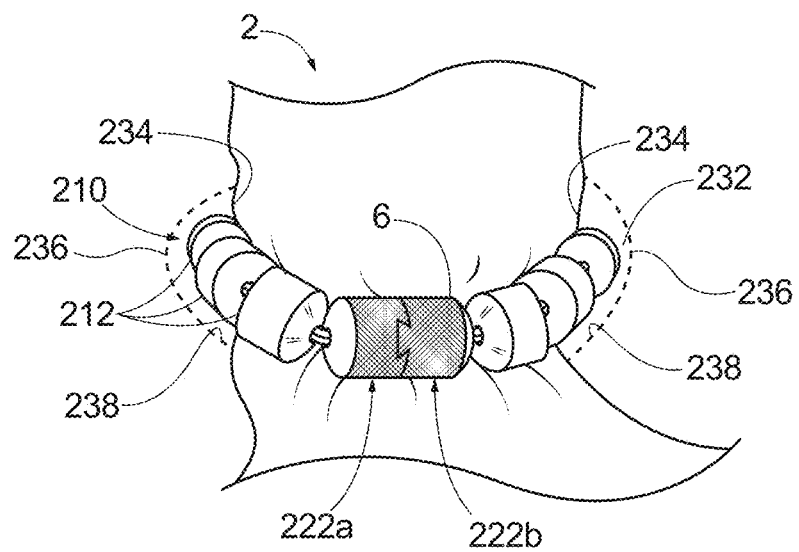
FIG. 9 depicts a perspective view of second exemplary alternative implantable sphincter assistance device, where the exterior wall of the LES has formed around the implantable sphincter assistance device to form a tissue capsule.
Figure 10:
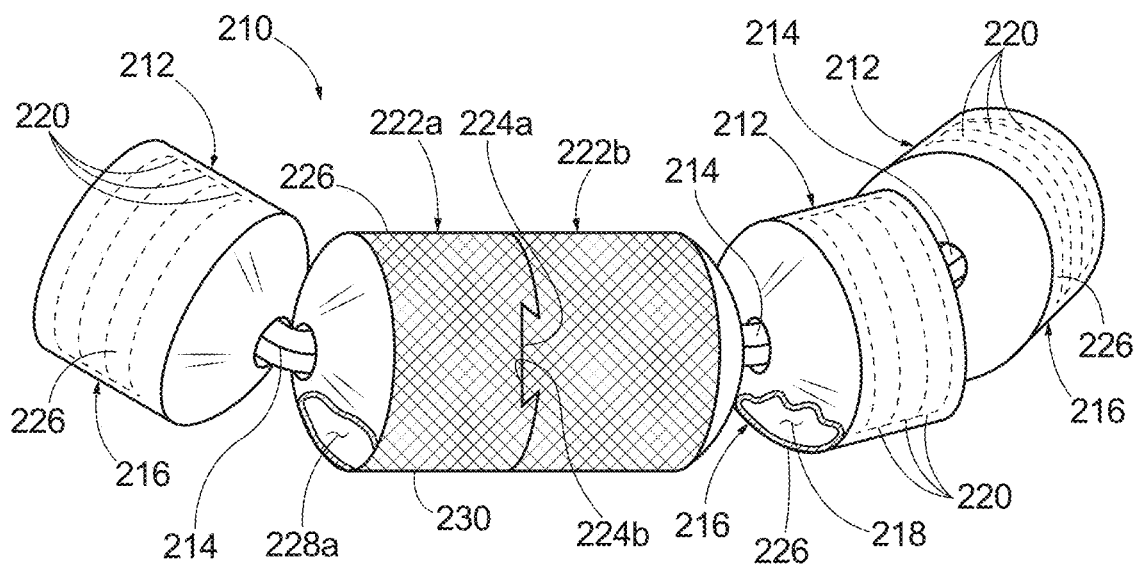
FIG. 10 depicts an enlarged perspective view of the implantable sphincter assistance device of FIG. 9 with the implantable sphincter assistance device including a plurality of beads, a flexible cord, and first and second clasps with respective coatings applied to each.

FIG. 9 shows a perspective view of a second exemplary alternative implantable sphincter assistance device (210). Similar to device (110) shown and described and above with reference to FIGS. 6-8, device (210) is sized and configured to surround an exterior wall (24) of LES (6). Device (210) includes a plurality of beads (212), at least one connector (shown as a flexible wire (214)), and secondary material (216) that at least partially surrounds at least a majority of beads (212). Beads (212) may be similar to beads (30) shown and described above with reference to FIGS. 3-5B. Each bead (212) includes an exterior surface (218) (shown as a cutaway portion of FIG. 10) which may be similar to the exterior surface of housing (32, 34) shown and described above with reference to FIGS. 3-5B. Beads (212) are shown as titanium beads; however, beads (212) may be formed from a variety of suitable materials. Beads (212) are configured to be individually moveable along flexible wire (214). For example, each bead (212) may be individually selectively moveable to a desired location. Each bead (212) includes a plurality of magnets (220) configured to impart a radially inwardly oriented magnetic bias. Similar to magnets (60) shown and described above with reference to FIGS. 4-5B, magnets (220) may be annular or toroidal rare-earth permanent magnets or another suitable magnet. Magnets (220) of beads (212) are configured to magnetically bias opening (7) of LES (6) to a closed configuration. Magnets (220) of beads (212) are also configured to permit separation of beads (212) to thereby permit passage of a bolus through opening (7) of LES (6).

Similar to FIG. 8B regarding device (210), exterior wall (11) of LES (6) has formed around device (210) to form a tissue capsule (232). Device (210) includes first and second clasps (222a-b) that are configured to transition between an unlocked configuration allowing for insertion and removal of device (210) to a locked configuration that radially surrounds LES (6). First and second clasps (222a-b) may be similar to fastener features (50) shown and described above with reference to FIGS. 5A-5B or first and second clasps (122a-b) shown and described above with reference to FIG. 6. First and second clasps (222a-b) include complementary attachment portions (224a-b) that are configured to interlock with each other in the locked configuration. First and second clasps (222a-b) include exterior surfaces (228a-b). Exterior surfaces (228a-b) of first and second clasps (222a-b) include a coating (230) to encourage bonding with tissue that is configured to anchored to exterior wall (11) of LES (6). It is envisioned that one or both of first and second clasps (222a-b) includes coating (230). Flexible wire (214) is configured to serially connect beads (212) to form a ring. While connector is shown as a flexible wire (214), it is also envisioned that connector may include a plurality of links (e.g. links (40) shown and described above with reference to FIGS. 4-5B) or any other suitable connector.

As shown in FIGS. 9-11B, secondary material (216) comprises a coating (226) applied to exterior surfaces (218) of beads (212) to discourage bonding with tissue and flexible wire (214). Secondary material (216) disposed on exterior surface (218) of beads (212) controls tissue remodeling around the outside of device (210). Coating (226) is configured to prevent tissue growth onto beads (212) that restricts motion of beads (212). In addition to coating (226) being applied to beads (212), the same or similar coating may be applied to flexible wire (214) to discourage bonding with tissue. This enables beads (212) to freely move along flexible wire (214).

Figure 11B:
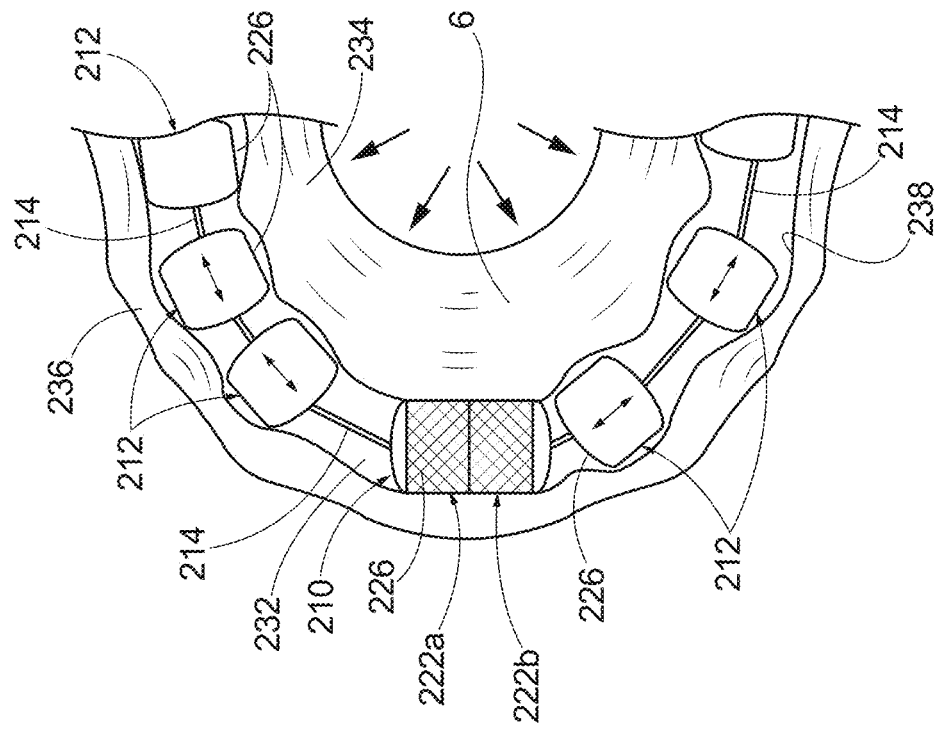
FIG. 11B depicts a top partial sectional view of the implantable sphincter assistance device similar to FIG. 11A with the first and second clasps coupled with the external wall of the LES, but with the beads in a second configuration.
Figure 11A:
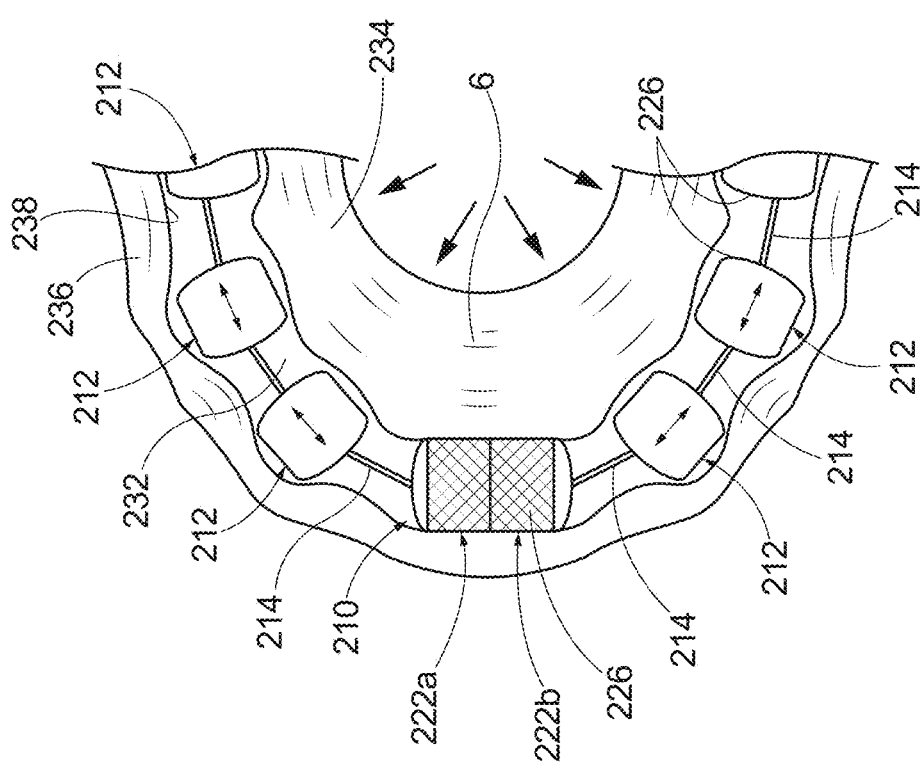
FIG. 11A depicts a top partial sectional view of the implantable sphincter assistance device of FIG. 9 implanted into the external wall of the LES, with the first and second clasps coupled with the external wall of the LES and the beads in a first configuration.

FIGS. 11A-11B show the free movement of beads (212) within tissue capsule (232), while coating (226) covering exterior surfaces (228a-b) of first and second clasps (222a-b) is coupled with inner surface (238) of tissue capsule (232). In other words, coating (226) fixably couples first and second clasps (222a-b) to inner surface (238) of tissue capsule (232) preventing relative movement. As shown, exterior wall (11) includes an inner wall portion (234) and an outer wall portion (236). As a result, beads (212) may freely move around inside tissue capsule (232). The tissue around the first and second clasps (222a-b) would secure beads (212) in place, while allowing beads (212) to freely travel on flexible wire (214). FIG. 11A shows a top partial sectional view of device (210) of FIG. 9 already implanted into exterior wall (11) of LES (6), with first and second clasps (222a-b) coupled with exterior wall (11) of LES (6) and beads (212) in a first configuration. FIG. 11B shows a top partial sectional view of device (210) similar to FIG. 11A with first and second clasps (222a-b) coupled with exterior wall (11) of LES (6), but with beads (212) in a second configuration. Passive modification of device (210) improves the mechanical interactions of device (210) with the surrounding tissue during remodeling and after healing has concluded. Surface property modification and coatings control tissue interaction with device (210). Surface properties (e.g. coating (226)) of beads (212) and/or flexible wire (214) discourages tissue attachment enabling beads (212) to freely move along flexible wire (214) to prevent tissue erosion.

C. Third Exemplary Alternative Implantable Sphincter Assistance Device

FIGS. 12A-14B show a third exemplary implantable sphincter assistance device (310). Similar to device (110) shown and described and above with reference to FIGS. 6-8, device (310) is sized and configured to surround an exterior wall (11) of LES (6). Device (310) includes a plurality of beads (312), at least one connector (shown as a flexible wire (314)), and secondary material (316) that at least partially surrounds beads (312). Beads (312) may be similar to beads (30) shown and described above with reference to FIGS. 3-5B. Each bead (312) includes an exterior surface (318) which may be similar to the exterior surface of housing (32, 34) shown and described above with reference to FIGS. 3-5B. Beads (312) are shown as titanium beads; however, beads (312) may be formed from a variety of suitable materials. Beads (312) are configured to be individually moveable along flexible wire (314). For example, each bead (312) may be individually selectively moveable to a desired location. Each bead (312) includes a plurality of magnets (320) configured to impart a radially inwardly oriented magnetic bias. Similar to magnets (60) shown and described above with reference to FIGS. 4-5B, magnets (320) may be annular or toroidal rare-earth permanent magnets or another suitable magnet. Magnets (320) of beads (312) are configured to magnetically bias opening (7) of LES (6) to a closed configuration. Magnets (320) of beads (312) are also configured to permit separation of beads (312) to thereby permit passage of a bolus through opening (7) of LES (6). Device (310) also includes first and second clasps (not shown) that are configured to transition between an unlocked configuration allowing for insertion and removal of device (310) to a locked configuration that radially surrounds LES (6). First and second clasps may be similar to fastener features (50) shown and described above with reference to FIGS. 5A-5B.

Figure 12A:
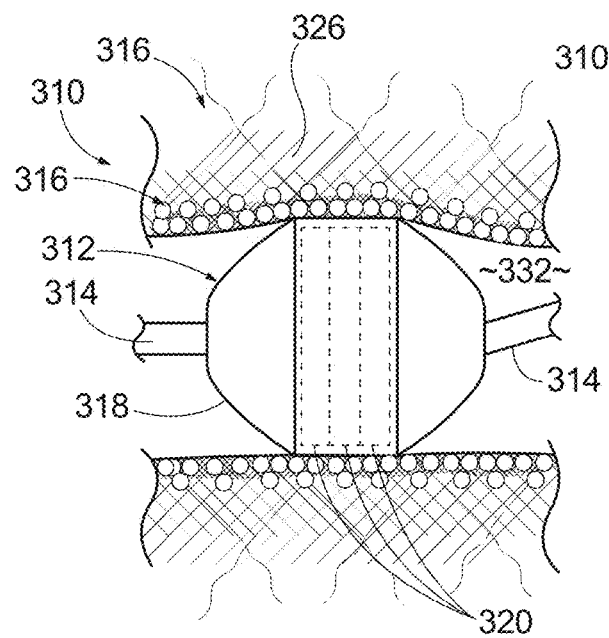
FIG. 12A depicts a top partial sectional view of a third exemplary alternative implantable sphincter assistance device that includes bioabsorbable scaffold.
Figure 13A:
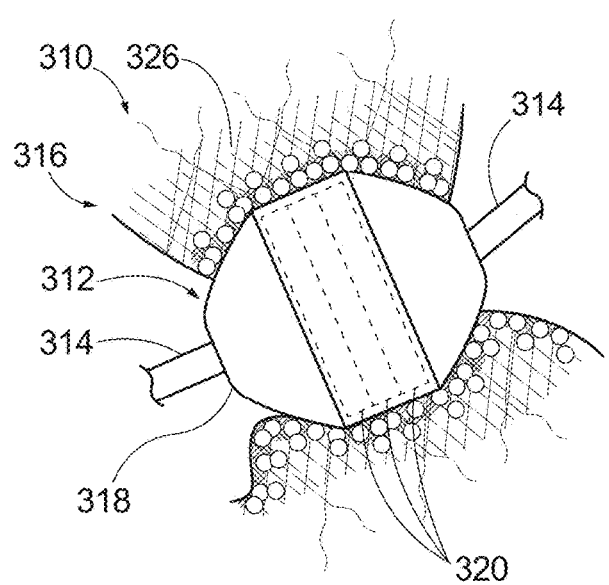
FIG. 13A depicts a top partial sectional view of the implantable sphincter assistance device of FIG. 12A.
Figure 14A:
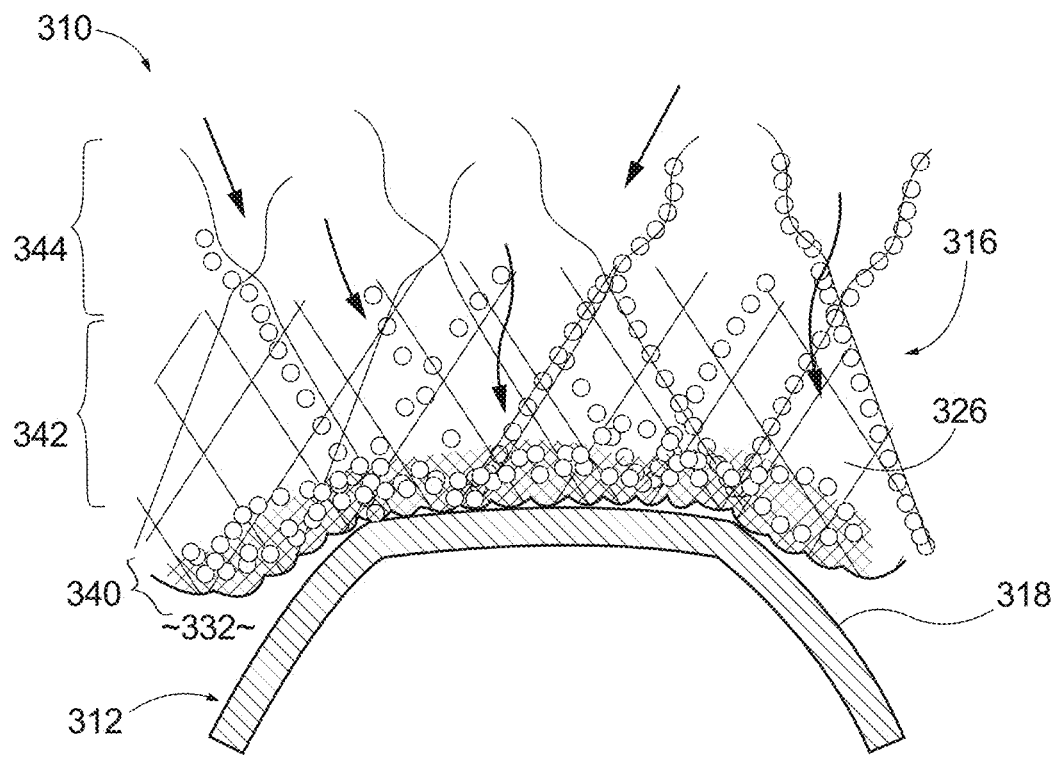
FIG. 14A depicts a top partial sectional view of the implantable sphincter assistance device of FIG. 12A.
Figure 14B:
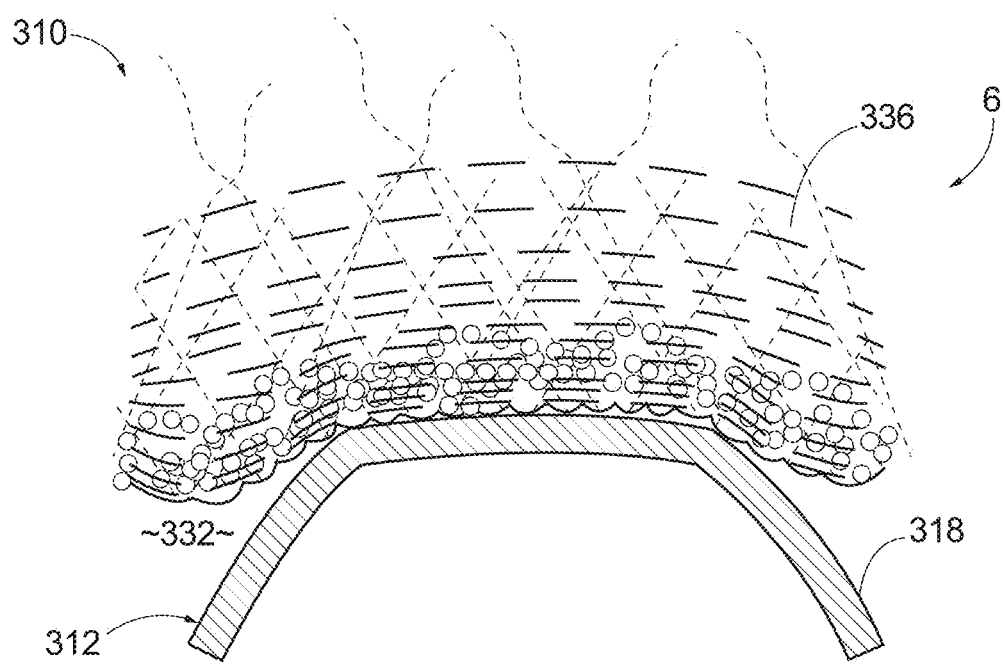
FIG. 14B depicts a sectional view of the implantable sphincter assistance device of FIG. 12B with the bioabsorbable scaffold having been absorbed resulting in tissue encapsulation.

As shown in FIGS. 12A, 13A, and 14A, secondary material (316) comprises a bioabsorbable scaffold (326). Bioabsorbable scaffold (326) encourages encapsulation of device (310) without restricting movement of device (310). FIG. 12A shows a top partial sectional view of device (310). Bioabsorbable scaffold (326) is configured to encapsulate a majority of beads (312), where bioabsorbable scaffold is configured to expand and contract. Bioabsorbable scaffold (326) may be formed from an absorbable polymer that includes PGA, PDS, PCL, or PLA or a copolymer blend of PGA, PDS, PCL, or PLA, where bioabsorbable scaffold (326) is configured to encourage cellular in growth. As shown according to an exemplary embodiment, bioabsorbable scaffold (326) includes a tight weave portion (340), a loose weave portion (342), and a frayed edge portion (344). As shown in FIGS. 14A-14B, bioabsorbable scaffold (326) transitions from tight weave portion (340), to loose weave portion (342), to frayed edge portion (344) moving away from exterior surface (318) of beads (312). In other words, on the side that contacts device (310) is a tighter weave (e.g. tight weave portion (340)), mid-substance is a more open but inter-woven area (e.g. loose weave portion (342)), further from device (310) is a loose fiber free side (e.g. frayed edge portion (344)). Tight weave portion (340), loose weave portion (342), and frayed edge portion (344) provide a tissue contacting surface that encourages cells to migrate into bioabsorbable scaffold (326).

Device (310) integrates absorbable materials to create short term remodeling scaffolds to influence the tissue remodeling around device (310). Bioabsorbable scaffold (326) controls the orientation and organization of the remodeled tissue while protecting the tissue before and during remodeling. Bioabsorbable scaffold (326) creates a tissue capsule (332) that causes less restriction on device (310) leading to reduced tissue erosion. Bioabsorbable scaffold (326) may be made of an absorbable polymer like PGA, PDS, PCL, or PLA or a copolymer blend of the materials. Alternatively, bioabsorbable scaffold (326) may be manufactured as a melt-blown non-woven, made as a mesh or film, lyophilized into a foam. Bioabsorbable scaffold (326) may include a multi polymer weave consisting of polyglactin 910 (a copolymer) and PDS (a monomer) or PGA threads. Bioabsorbable scaffold (326) serves as a short-term remodeling scaffold for improved tissue in growth. For example, bioabsorbable scaffold (326) may ideally be fully structural for the first few days or weeks, and then would degrade in sections allowing the cells to replace the absorbable sections.

Figure 12B:
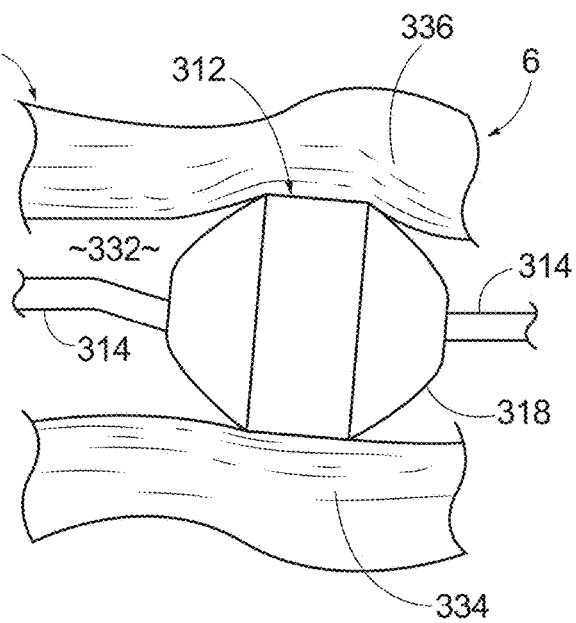
FIG. 12B depicts a top partial sectional view of the implantable sphincter assistance device of FIG. 12A, but after the bioabsorbable scaffold has been absorbed resulting in tissue encapsulation.
Figure 13B:
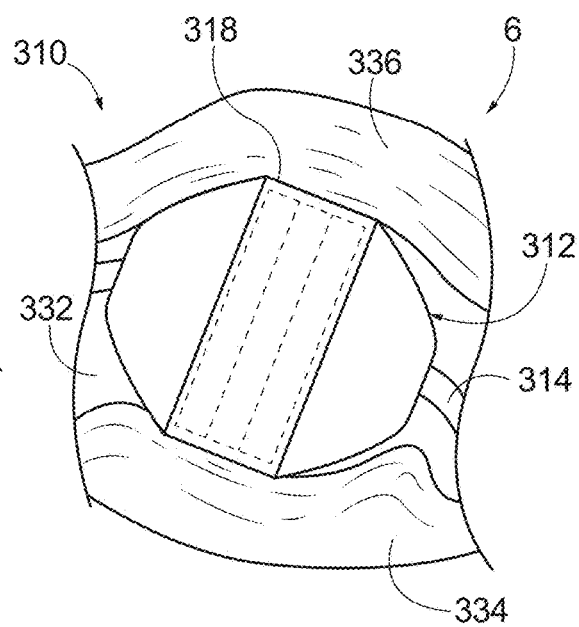
FIG. 13B depicts a top partial sectional view of the implantable sphincter assistance device of FIG. 12B surrounded by tissue.

As shown in FIGS. 12B, 13B, and 14B, bioabsorbable scaffold (326) already been absorbed by exterior wall (11) of LES (6) to form tissue capsule (332) (similar to FIG. 8 regarding device (110)). Exterior wall (11) includes an inner wall portion (334) and an outer wall portion (336). FIGS. 12B and 13B show top partial sectional views of device (310) of FIGS. 12A and 13A, but after bioabsorbable scaffold (326) has been absorbed resulting in tissue encapsulation. FIG. 14B shows an enlarged sectional view of device (310) of FIG. 12B with bioabsorbable scaffold (326) having been absorbed resulting in tissue encapsulation. Tissue capsule (332) is configured to have an inner surface (338) that is separated a distance from bead (312) allowing majority of beads (312) to freely move around inside tissue capsule (332).

D. Fourth Exemplary Alternative Implantable Sphincter Assistance Device

FIGS. 15-17B show a fourth exemplary alternative implantable sphincter assistance device (410). Similar to device (110) shown and described and above with reference to FIGS. 6-8, device (410) is sized and configured to surround an exterior wall (11) of LES (6). Device (410) includes a plurality of beads (412), at least one connector (shown as a flexible wire (414)), and secondary material (416) that at least partially surrounds at least a majority of beads (412). Beads (412) may be similar to beads (30) shown and described above with reference to FIGS. 3-5B. Each bead (412) includes an exterior surface (418) which may be similar to the exterior surface of housing (32, 34) shown and described above with reference to FIGS. 3-5B. Beads (412) are shown as titanium beads; however, beads (412) may be formed from a variety of suitable materials. Beads (412) are configured to be individually moveable along flexible wire (414). For example, each bead (412) may be individually selectively moveable to a desired location. Each bead (412) includes a plurality of magnets (420) configured to impart a radially inwardly oriented magnetic bias. Similar to magnets (60) shown and described above with reference to FIGS. 4-5B, magnets (420) may be annular or toroidal rare-earth permanent magnets or another suitable magnet. Magnets (420) of beads (412) are configured to magnetically bias opening (7) of LES (6) to a closed configuration. Magnets (420) of beads (412) are also configured to permit separation of beads (412) to thereby permit passage of a bolus through opening (7) of LES (6).

While not shown, device (410) may also include first and second clasps similar to fastener features (50) shown and described above with reference to FIGS. 5A-5B. Clasps are configured to transition between an unlocked configuration allowing for insertion and removal of device (410) to a locked configuration that radially surrounds LES (6). Flexible wire (414) is configured to serially connect beads (412) to form a ring. While connector is shown as flexible wire (414), it is also envisioned that connector may include a plurality of links (e.g. links (40) shown and described above with reference to FIGS. 4-5B) or any other suitable connector.

Figure 15:
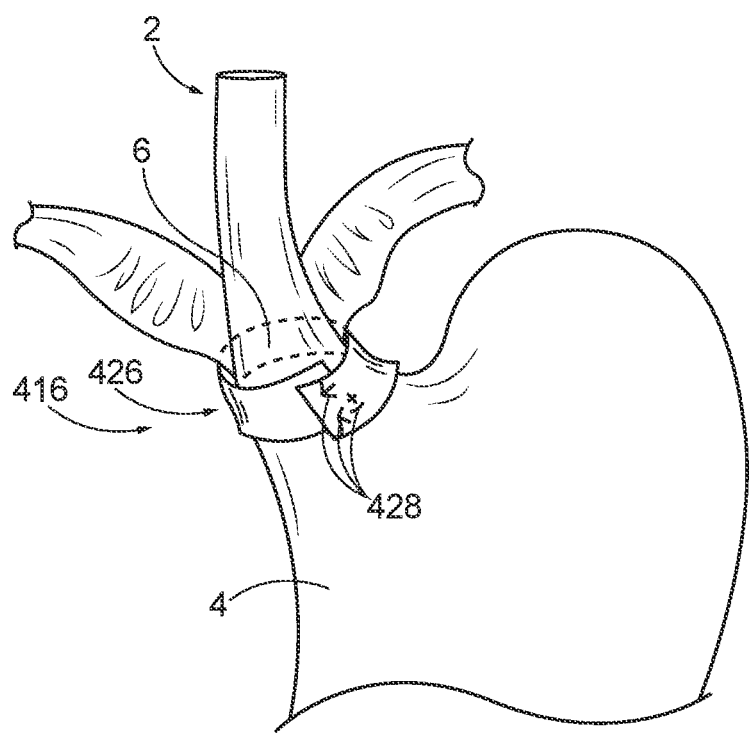
FIG. 15 depicts a perspective view of an exemplary bioabsorbable reinforcement buttress sutured around the exterior wall of the LES using sutures.

Secondary material (416) includes a bioabsorbable reinforcement buttress (426) that is configured to surround at least a portion of exterior wall (11) of LES (6) prior to insertion of device (410). Secondary material (416) is configured to promote scar tissue formation to prevent tissue erosion that might otherwise be caused by device (410). FIG. 15 shows a perspective view of bioabsorbable reinforcement buttress (426) sutured around exterior wall of LES using one or more sutures (428).

Bioabsorbable reinforcement buttress (426) may be treated with one or more therapeutic substances. The therapeutic substances may include an agent configured to heal tissue from a disease, defect, infection, inflammation, trauma, or any combination thereof. The therapeutic substances may include an agent configured to physically protect tissue from acidic compounds, such as agents that act to neutralize an acidic compound. The therapeutic substances may include a drug, a steroid, an antibiotic, or any other suitable substance that would be apparent to one having ordinary skill in the art in view of the teachings herein. Non-limiting examples of therapeutic substances may include antimicrobial agents, antifungal agents, anti-inflammatory agents, and growth factors. Non-limiting examples of antimicrobial agents include Ionic Silver, Triclosan, Tetracyclines, Doxycycline, Minocycline, Demeclocycline, Tetracycline, Oxytetracycline, Gentamicin, Neomycin, Non-limiting examples of antifungal and antimicrobial agents include Triclosan, Triazole, Thiazole, LAE, Sodium Stearate. Non-limiting examples of anti-inflammatory agents include non-steroidal anti-inflammatory agents (e.g., Salicylates, Aspirin, Diflunisal, Propionic Acid Derivatives, Ibuprofen, Naproxen, Fenoprofen, and Loxoprofen), acetic acid derivatives (e.g., Tolmetin, Sulindac, and Diclofenac), enolic acid derivatives (e.g., Piroxicam, Meloxicam, Droxicam, and Lornoxicam), anthranilic acid derivatives (e.g., Mefenamic Acid, Meclofenamic Acid, and Flufenamic Acid), selective COX-2 inhibitors (e.g., Celecoxib (Celebrex), Parecoxib, Rofecoxib (Vioxx), Sulfonanilides, Nimesulide, and Clonixin), immune selective anti-inflammatory derivatives, corticosteroids (e.g., Dexamethasone), and iNOS inhibitors. Non-limiting examples of growth factors include those that are cell signaling molecules that stimulate cell growth, healing, remodeling, proliferation, and differentiation. Exemplary growth factors can be short-ranged (paracrine), long ranged (endocrine), or self-stimulating (autocrine). Further examples of the growth factors include growth hormones (e.g., a recombinant growth factor, Nutropin, Humatrope, Genotropin, Norditropin, Saizen, Omnitrope, and a biosynthetic growth factor), Epidermal Growth Factor (EGF) (e.g., inhibitors, Gefitinib, Erlotinib, Afatinib, and Cetuximab), heparin-binding EGF like growth factors (e.g., Epiregulin, Betacellulin, Amphiregulin, and Epigen), Transforming Growth Factor alpha (TGF-a), Neuroregulin 1-4, Fibroblast Growth Factors (FGFs) (e.g., FGF1-2, FGF2, FGF11-14, FGF18, FGF15/19, FGF21, FGF23, FGF7 or Keratinocyte Growth Factor (KGF), FGF10 or KGF2, and Phenytoin), Insuline-like Growth Factors (IGFs) (e.g., IGF-1, IGF-2, and Platelet Derived Growth Factor (PDGF)), Vascular Endothelial Growth Factors (VEGFs) (e.g., inhibitors, Bevacizumab, Ranibizumab, VEGF-A, VEGF-B, VEGF-C, VEGF-D and Becaplermin). The therapeutic substances may also include other medicants, such examples may also be further constructed and operable in accordance with at least some of the teachings of U.S. Pub. No. 2017/0055986, entitled "Medicant Eluting Adjuncts and Methods of Using Medicant Eluting Adjuncts," published Mar. 2, 2017, issued as U.S. Pat. No. 10,569,071 on Feb. 25, 2020, the disclosure of which is incorporated by reference herein.

Figure 16A:
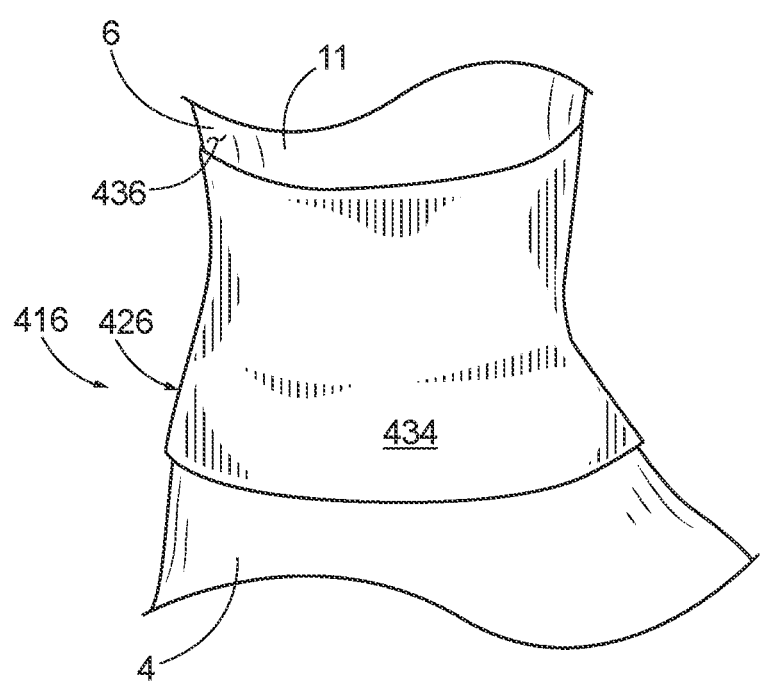
FIG. 16A depicts an enlarged perspective view of the bioabsorbable reinforcement buttress coupled around the exterior wall of the LES.
Figure 16B:
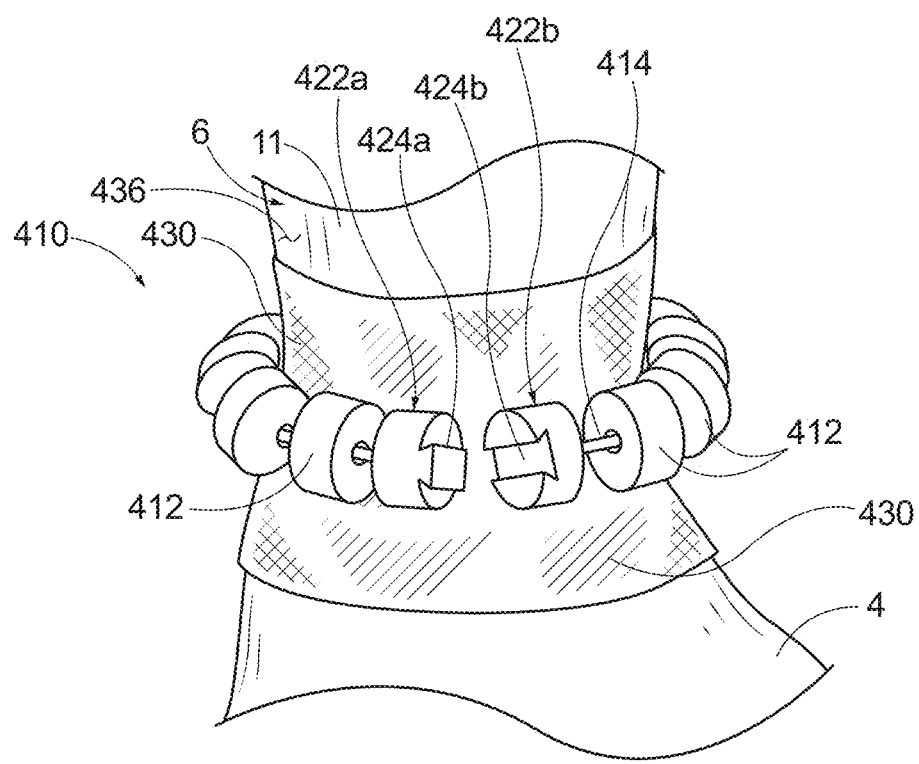
FIG. 16B depicts an enlarged perspective view of the bioabsorbable reinforcement buttress absorbed into the exterior wall of the LES with a fourth exemplary alternative implantable sphincter assistance device being inserted around the exterior wall of the LES.
Figure 16C:
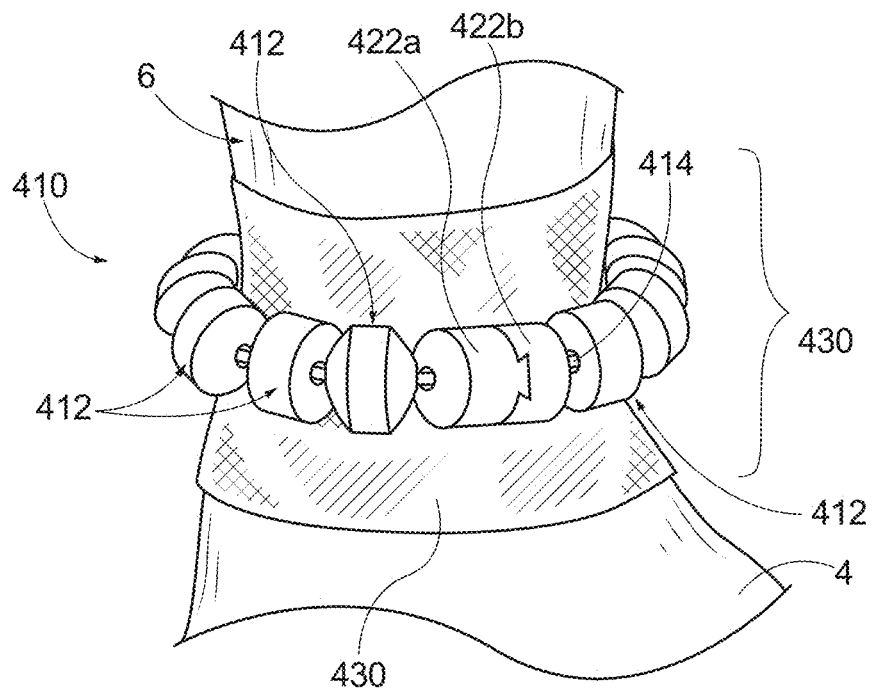
FIG. 16C depicts an enlarged perspective view of the bioabsorbable reinforcement buttress absorbed into the exterior wall of the LES with a fifth exemplary alternative implantable sphincter assistance device already inserted around the exterior wall of the LES.
Figure 17A:
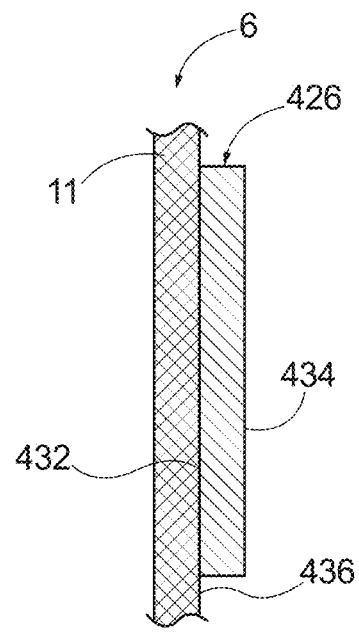
FIG. 17A depicts a side sectional view of a portion of the bioabsorbable reinforcement buttress coupled around the exterior wall of the LES of FIG. 16A.

FIGS. 16A-16C show an exemplary method of implanting device (410). FIG. 16A shows an enlarged perspective view of bioabsorbable reinforcement buttress (426) coupled around at least a portion of exterior wall (11) of LES (6). The method also includes waiting a period of time for exterior wall (11) of LES (6) to bioabsorb bioabsorbable reinforcement buttress (426) producing scar tissue (430). Scar tissue (430) prevents device (410) from causing tissue erosion. FIG. 17A shows a side sectional view of bioabsorbable reinforcement buttress (426) coupled around exterior wall (11) of LES (6) of FIG. 16A. As shown, bioabsorbable reinforcement buttress (426) includes opposing first and second sides (432, 434), where first side (432) is coupled with outer surface (436) of exterior wall (11).

Figure 17B:
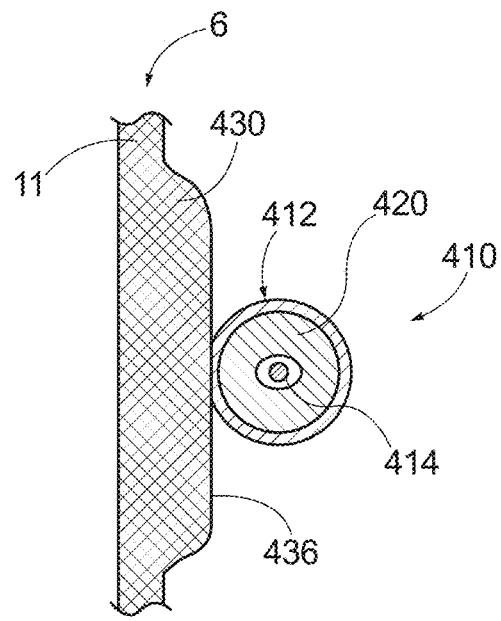
FIG. 17B depicts a side sectional view of the bioabsorbable reinforcement buttress absorbed into the exterior wall of the LES with and the implantable sphincter assistance device of FIG. 16B disposed adjacent the resulting scar tissue.

FIG. 16B shows an enlarged perspective view of bioabsorbable reinforcement buttress (426) absorbed into exterior wall (11) of LES (6) with device (410) being inserted around exterior wall (11) of LES (6). First and second clasps (422a-b) of device (410) are coupled together to serially connect beads (412) to form a ring. FIG. 16C shows an enlarged perspective view of bioabsorbable reinforcement buttress (426) absorbed into exterior wall (11) of LES (6) with device (410) already inserted around exterior wall (11) of LES (6). FIG. 17B shows a side sectional view of bioabsorbable reinforcement buttress absorbed into exterior wall (11) of LES (6) with device (410) of FIG. 16C.

As shown in FIGS. 15-17B, combination of surface features or absorbable polymer integration to provides a therapeutic or bio-active material that can be used to influence the remodeling of the tissue around device (410) (e.g. beads (412)). Bioabsorbable reinforcement buttress (426) is added between esophagus and bead (412), where the bioabsorbable reinforcement buttress (426) may be treated with one or more therapeutic agent to reduce trauma and/or improve patient recovery. Applyable adjunct material (e.g. bioabsorbable reinforcement buttress (426)) to controlled release healing impact agent on device (410). Applyable adjunct material provides controlled release healing impacting agents on device (410). Bioabsorbable reinforcement buttress (426) may be either a form that allows the tissue to grow into bioabsorbable reinforcement buttress (426) like melt-blown non-woven PGA, PCL, PLA, PDS materials or any copolymer of them. Likewise, bioabsorbable reinforcement buttress (426) may be constructed in such a way as to inhibit tissue in-growth into the buttress like a film or non-porous absorbable construct.

Bioabsorbable reinforcement buttress (426) may be configured to be non-absorbable material, e.g. nylon, PEEK, or silicone. It is envisioned that bioabsorbable reinforcement buttress (426) may be attached to beads (412) or spacers, or bioabsorbable reinforcement buttress (426) may be a sleeve or layer between device (410) and the tissue contact plane, while not being part of the device (410) itself, so that device (410) may freely slide.

E. Fifth Exemplary Alternative Implantable Sphincter Assistance Device

FIGS. 18A-18B show a fifth exemplary alternative implantable sphincter assistance device (510). Similar to device (110) shown and described and above with reference to FIGS. 6-8, device (510) is sized and configured to surround an exterior wall (11) of LES (6). Device (510) includes a plurality of beads (512) (an outer surface of one such bead being shown, at least one connector (similar to links (40) or flexible wire (114)), and secondary material (516) that at least partially surrounds beads (512). Beads (512) may be similar to beads (30) shown and described above with reference to FIGS. 3-5B. Each bead (512) includes an exterior surface (518) which may be similar to the exterior surface of housing (32, 34) shown and described above with reference to FIGS. 3-5B. Beads (512) are shown as titanium beads.

FIGS. 18A-18B are microscopic views of an exemplary Knoop hardness test to show how exterior surface (518) of bead (512) may be modified to improve organometallic bonding. The Knoop hardness test is a microhardness test that used particularly for brittle materials or thin sheets, where only a small indentation may be made for testing purposes. A pyramidal diamond point may be pressed into the polished surface of the test material with a known (e.g., 100-gram) load, for a specified dwell time, and the resulting indentation may be measured using a microscope. Microhardness indentations may be made with a Knoop indenter using a 100-gram load except where otherwise indicated.

FIG. 18A shows an enlarged sectional view of bead (512) where secondary material (516) comprises a coating that is applied without the use of a shielding gas. In other words, FIG. 18A shows a polished cross-section of a CP titanium test weld with no shielding gas. FIG. 18A shows three zones that include a melted zone (520), a recrystallized zone (522), and a base metal zone (524). As shown, load (526) results in a 150.8 HK, load (528) results in a 151.1 HK, load (530) results in a 149.4 HK, load (532) results in a 197.5 HK, load (534) results in a 207.6 HK, load (536) results in a 295.0 HK, and load (538) results in a 746.5 HK. FIG. 18A shows a crack (540) in center of weld (542). Chemical etch times are similar to the conditions used on bead (512) that had shielding gas applied (FIG. 18A). Depth of the etch in melted zone (520) may be due to increased levels of oxygen, which may also result in the extreme high hardness and cracking.

FIG. 18B shows an enlarged sectional view of bead (512) where a coating is applied with the use of a shielding gas. In other words, FIG. 18B shows a polished cross-section of a CP titanium test weld with a shielding gas applied. FIG. 18B also shows melted zone (544), recrystallized zone (546), and base metal zone (548). As shown, load (550) results in a 141.9 HK, load (552) results in a 146.0 HK, load (554) results in a 149.0 HK, load (556) results in a 142.5 HK (using a 200 gram load), load (558) results in a 143.4 HK (using a 200 gram load), load (660) results in a 173.3 HK, load (562) results in a 228.5 HK, load (564) results in a 197.2 HK, load (566) results in a 232.6 HK, load (568) results in a 278.8 HK, load (570) results in a 270.8 HK, and load (572) results in a 262.4 HK.

At least one of beads (512) may be formed from polycrystalline titanium, where secondary material (516) is configured to oxidize polycrystalline titanium to improve organometallic bonding. It is envisioned that a majority or each bead may be formed from polycrystalline titanium, where secondary material (516) is configured to oxidize polycrystalline titanium to improve organometallic bonding. Controlled surface modification in titanium produces reliable covalent bonds of organic and organometallic compounds. The compounds may create adhesion resistance or promote tissue attachment. The compounds may also impact the frictional characteristics of device (510) with respect to the encapsulation of the remodeled tissue. Increasing the friction causes bead (512) to move less freely within the tissue encapsulation. However, friction and tissue interaction could be minimized thereby minimizing the "feeling" of motion of device (510) to the user or pain felt as device (510) repeatedly opens and closes.

To improve covalent bonding, the native oxide/hydroxide surface may be influenced to have a higher coverage of hydroxy (OH) groups. This may be achieved through thermal control during the oxidation process. Oxygen (O), nitric oxide (NO), and carbon monoxide (CO) may be used to oxidize titanium to a range of oxidation states (4+, 3+, and 2+, respectively) under similar and pressure conditions. The titanium dioxide (TiO2) chemical composition interface is created by temperature (e.g., ranging from approximately 450K to approximately 650K, or more particularly from approximately 550K to approximately 600K). The desired hydroxyl species may generally occur most frequently between 250K and 350K. Based on these two opposed conditions, the maximum OH concentration may be achieved at 550K, while also creating the desired outer surface with the desired crystallinity. At this oxidation temperature, up to 16% of the surface oxygen may be of the desired OH species.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An implantable sphincter assistance device configured to surround an exterior wall of an esophagus, wherein the implantable sphincter assistance device comprises: (a) a plurality of beads, wherein each of the beads has an exterior surface; (b) at least one connector configured to serially connect the beads to form a ring; and (c) secondary material configured to be disposed between the exterior surface of at least one of the beads and the exterior wall of the esophagus, wherein the secondary material is configured to control remodeling of tissue surrounding the exterior wall of the esophagus.

Example 2

The implantable sphincter assistance device of Example 1, wherein the secondary material is configured to be disposed between the exterior surface of a majority of the beads and the exterior wall of the esophagus.

Example 3

The implantable sphincter assistance device of Example 2, wherein the secondary material comprises a bioabsorbable casing coupled with the exterior surface of the majority of the beads, wherein the bioabsorbable casing is configured to be absorbed by the exterior wall to form a tissue capsule, wherein the tissue capsule is configured to have an inner wall that is separated a distance from the beads allowing the majority of the beads to freely move around inside the tissue capsule.

Example 4

The implantable sphincter assistance device of Example 3, wherein the bioabsorbable casing extends radially outwardly from the exterior surface of the majority of the beads, wherein the bioabsorbable casing is configured to be absorbed by the exterior wall to form the tissue capsule.

Example 5

The implantable sphincter assistance device of Examples 3 or 4, wherein the bioabsorbable casing includes a tapered lead in portion and a raised body portion surrounding a primary circumference of the majority of the beads.

Example 6

The implantable sphincter assistance device of any one or more of Examples 1 through 5, wherein the connector comprises a flexible cord, wherein the beads are configured to be individually moveable along the flexible cord, wherein the flexible cord and the beads include a coating configured to discourage bonding with the tissue.

Example 7

The implantable sphincter assistance device of any one or more of Examples 1 through 6, further comprising first and second clasps that are configured to transition from an unlocked configuration allowing for insertion and removal of the implantable sphincter assistance device and a locked configuration that radially surrounds the esophagus, wherein the first and second clasps include exterior surfaces, wherein the exterior surfaces of the first and second clasps include a coating to encourage bonding with the tissue that is configured to anchored to the exterior wall.

Example 8

The implantable sphincter assistance device of any one or more of Examples 1 through 7, wherein the beads are titanium beads, wherein the secondary material includes a coating coupled with the exterior surface of the titanium beads.

Example 9

The implantable sphincter assistance device of any one or more of Examples 2 through 8, wherein the secondary material includes a bioabsorbable scaffold, wherein the bioabsorbable scaffold is configured to encapsulate the majority of the beads, wherein the bioabsorbable scaffold is configured to expand and contract.

Example 10

The implantable sphincter assistance device of Example 9, wherein the bioabsorbable scaffold is formed from absorbable polymer that includes PGA, PDS, PCL, or PLA or a copolymer blend of PGA, PDS, PCL, or PLA, wherein the bioabsorbable scaffold is configured to encourage cellular in growth.

Example 11

The implantable sphincter assistance device of Examples 9 or 10, wherein the bioabsorbable scaffold includes a tight weave, a loose weave, and a frayed edge, wherein the bioabsorbable scaffold transitions from the tight weave, to the loose weave, to the frayed edge moving away for the exterior surface of the majority of the beads.

Example 12

The implantable sphincter assistance device of any one or more of Examples 9 through 11, wherein the bioabsorbable scaffold encourages encapsulation of the implantable sphincter assistance device without restricting movement of the implantable sphincter assistance device.

Example 13

The implantable sphincter assistance device of any one or more of Examples 1 through 12, wherein the secondary material includes a bioabsorbable reinforcement buttress that is configured to surround at least a portion of the exterior wall of the esophagus prior to insertion of the artificial sphincter, wherein secondary material is configured to promote scar tissue formation to prevent tissue erosion caused by the artificial sphincter.

Example 14

The implantable sphincter assistance device of Example 13, wherein the bioabsorbable reinforcement buttress is treated with one or more therapeutic substances.

Example 15

The implantable sphincter assistance device of any one or more of Examples 1 through 14, wherein at least one of the beads is formed from polycrystalline titanium, wherein the secondary material is configured to oxidize the polycrystalline titanium to improve organometallic bonding.

Example 16

The implantable sphincter assistance device of any one or more of Examples 1 through 15, wherein each of the beads includes plurality of annular or toroidal rare-earth permanent magnets configured to impart a radially inwardly oriented magnetic bias to the ring, wherein the implantable sphincter assistance device is sized and configured to fit around a lower esophageal sphincter of the esophagus, wherein the magnets of the beads are configured to magnetically bias an opening of the lower esophageal sphincter to a closed configuration, wherein the magnets of the beads are configured to permit separation of the beads to thereby permit passage of a bolus through the opening of the lower esophageal sphincter.

Example 17

A method of implanting a sphincter assistance device, comprising: (a) providing a sphincter assistance device comprising: (i) a plurality of beads, wherein each of the beads has an exterior surface, (ii) at least one connector configured to serially connect the beads to form a ring, and (iii) bioabsorbable secondary material coupled to the exterior surface of a majority of the beads; and (b) inserting the sphincter assistance device around an exterior wall of an esophagus, wherein the bioabsorbable secondary material is absorbed by an exterior wall of an esophagus creating a tissue capsule having a greater volume than the artificial sphincter, wherein the greater volume allows for movement of the majority of the beads.

Example 18

The method of Example 17, wherein the bioabsorbable secondary material includes a bioabsorbable casing coupled with the exterior surface of a majority of the beads or a bioabsorbable scaffold, wherein the bioabsorbable secondary material is configured to control remodeling of the tissue surrounding the exterior wall of the esophagus.

Example 19

A method of implanting a sphincter assistance device, comprising: (a) coupling a bioabsorbable reinforcement buttress around at least a portion of an exterior wall of an esophagus; (b) waiting a period of time for the exterior wall of the esophagus to bioabsorb the bioabsorbable reinforcement buttress producing scar tissue; and (c) inserting the sphincter assistance device by coupling first and second clasp members of the sphincter assistance device together to serially connect a plurality of beads to the artificial sphincter, wherein the scar tissue prevents sphincter assistance device form causing tissue erosion.

Example 20

The method of Example 19, wherein each of the beads comprises a plurality of annular or toroidal rare-earth permanent magnets configured to impart a radially inwardly oriented magnetic bias to the beads to reinforce a sphincter to transition between a closed configuration and an open configuration.

IV. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An implantable sphincter assistance device configured to surround an exterior wall of an esophagus, wherein the implantable sphincter assistance device comprises:
    (a) a plurality of beads, wherein each of the beads has an exterior surface;
    (b) at least one connector configured to serially connect the beads to form a ring; and
    (c) a secondary material including a bioabsorbable casing that is configured to be disposed between the exterior surface of at least one of the beads and the exterior wall of the esophagus, wherein the bioabsorbable casing includes a tapered lead in portion and a raised body portion surrounding a primary circumference of a majority of the beads, wherein the tapered lead in portion is configured to resist movement of the implantable sphincter assistance device, wherein the secondary material is configured to control remodeling of tissue surrounding the exterior wall of the esophagus.

2. The implantable sphincter assistance device of claim 1, wherein the secondary material is configured to be disposed between the exterior surface of the majority of the beads and the exterior wall of the esophagus.

3. The implantable sphincter assistance device of claim 2, wherein the bioabsorbable casing is coupled with the exterior surface of the majority of the beads, wherein the bioabsorbable casing is configured to be absorbed by the exterior wall to form a tissue capsule, wherein the tissue capsule is configured to have an inner wall that is separated a distance from the beads allowing the majority of the beads to freely move around inside the tissue capsule.

4. The implantable sphincter assistance device of claim 3, wherein the bioabsorbable casing extends radially outwardly from the exterior surface of the majority of the beads, wherein the bioabsorbable casing is configured to be absorbed by the exterior wall to form the tissue capsule.

5. The implantable sphincter assistance device of claim 2, wherein the secondary material includes a bioabsorbable scaffold, wherein the bioabsorbable scaffold is configured to encapsulate the majority of the beads, wherein the bioabsorbable scaffold is configured to expand and contract.

6. The implantable sphincter assistance device of claim 5, wherein the bioabsorbable scaffold is formed from absorbable polymer that includes PGA, PDS, PCL, or PLA or a copolymer blend of PGA, PDS, PCL, or PLA, wherein the bioabsorbable scaffold is configured to encourage cellular in growth.

7. The implantable sphincter assistance device of claim 5, wherein the bioabsorbable scaffold includes a tight weave, a loose weave, and a frayed edge, wherein the bioabsorbable scaffold transitions from the tight weave, to the loose weave, to the frayed edge moving away from the exterior surface of the majority of the beads.

8. The implantable sphincter assistance device of claim 5, wherein the bioabsorbable scaffold is configured to encourage tissue encapsulation of the implantable sphincter assistance device without restricting movement of the implantable sphincter assistance device.

9. The implantable sphincter assistance device of claim 1, wherein the connector comprises a flexible cord, wherein the beads are configured to be individually moveable along the flexible cord, wherein the flexible cord and the beads include a coating configured to discourage bonding with the tissue.

10. The implantable sphincter assistance device of claim 1, further comprising first and second clasps that are configured to transition from an unlocked configuration allowing for insertion and removal of the implantable sphincter assistance device and a locked configuration that radially surrounds the esophagus, wherein the first and second clasps include exterior surfaces, wherein the exterior surfaces of the first and second clasps include a coating to encourage bonding with the tissue that is configured to be anchored to the exterior wall.

11. The implantable sphincter assistance device of claim 1, wherein the beads are titanium beads, wherein the secondary material includes a coating coupled with the exterior surface of the titanium beads.

12. The implantable sphincter assistance device of claim 1, wherein at least one of the beads is formed from polycrystalline titanium, wherein the secondary material is configured to oxidize the polycrystalline titanium.

13. The implantable sphincter assistance device of claim 1, wherein each of the beads includes plurality of annular or toroidal rare-earth permanent magnets configured to impart a radially inwardly oriented magnetic bias to the ring, wherein the implantable sphincter assistance device is sized and configured to fit around a lower esophageal sphincter of the esophagus, wherein the magnets of the beads are configured to magnetically bias an opening of the lower esophageal sphincter to a closed configuration, wherein the magnets of the beads are configured to permit separation of the beads to thereby permit passage of a bolus through the opening of the lower esophageal sphincter.

14. The implantable sphincter assistance device of claim 1, wherein at least one of the plurality of beads is configured to move along the at least one connector relative to the connector.

15. The implantable sphincter assistance device of claim 1, wherein the bioabsorbable casing is configured to extend completely around a perimeter formed by the exterior surface of at least one of the beads and the exterior wall of the esophagus.

16. The implantable sphincter assistance device of claim 15, wherein the perimeter defines a circumference, wherein the bioabsorbable casing is configured to extend completely around the circumference formed by the exterior surface of at least one of the beads and the exterior wall of the esophagus.

17. A method of implanting a sphincter assistance device, comprising:
    (a) providing a sphincter assistance device comprising:
        (i) a plurality of beads, wherein each of the beads has an exterior surface,
        (ii) at least one connector configured to serially connect the beads to form a ring, and
        (iii) bioabsorbable secondary material coupled to the exterior surface of a majority of the beads; and
    (b) inserting the sphincter assistance device around an exterior wall of an esophagus so that the bioabsorbable secondary material contacts the exterior wall of the esophagus, wherein the bioabsorbable secondary material is absorbed by an exterior wall of an esophagus creating a tissue capsule having a greater volume than the sphincter assistance device, wherein the greater volume allows for movement of the majority of the beads.

18. The method of claim 17, wherein the bioabsorbable secondary material includes a bioabsorbable casing coupled with the exterior surface of a majority of the beads or a bioabsorbable scaffold, wherein the bioabsorbable secondary material is configured to control remodeling of the tissue surrounding the exterior wall of the esophagus.

19. A method of implanting a sphincter assistance device, comprising:
(a) coupling a bioabsorbable reinforcement buttress around at least a portion of an exterior wall of an esophagus;
(b) waiting a period of time for the exterior wall of the esophagus to bioabsorb the bioabsorbable reinforcement buttress producing scar tissue; and
(c) inserting the sphincter assistance device around the exterior wall of the esophagus by coupling first and second clasp members of the sphincter assistance device together to serially connect a plurality of beads of the sphincter assistance device, wherein the scar tissue prevents the sphincter assistance device from causing tissue erosion.

20. The method of claim 19, wherein each of the beads comprises a plurality of annular or toroidal rare-earth permanent magnets configured to impart a radially inwardly oriented magnetic bias to the beads to reinforce a sphincter to transition between a closed configuration and an open configuration.

* * * * *